(12) United States Patent
Thiel et al.

(10) Patent No.: US 11,678,935 B2
(45) Date of Patent: *Jun. 20, 2023

(54) ENERGY DELIVERY SYSTEMS AND USES THEREOF

(71) Applicant: Neuwave Medical, Inc., Madison, WI (US)

(72) Inventors: Matthew Thiel, Verona, WI (US); Mark Thom, Madison, WI (US); Richard W. Schefelker, Madison, WI (US); Jeff Bissing, Madison, WI (US); Yaniv Lazimy, Madison, WI (US); Matt Schaning, Madison, WI (US); Dave Anderson, Madison, WI (US)

(73) Assignee: Neuwave Medical, Inc., Madison, WI (US)

(*) Notice: Subject to any disclaimer, the term of this patent is extended or adjusted under 35 U.S.C. 154(b) by 149 days.

This patent is subject to a terminal disclaimer.

(21) Appl. No.: 17/205,799

(22) Filed: Mar. 18, 2021

(65) Prior Publication Data
US 2021/0220050 A1 Jul. 22, 2021

Related U.S. Application Data

(63) Continuation of application No. 15/335,155, filed on Oct. 26, 2016, now Pat. No. 10,952,792.
(Continued)

(51) Int. Cl.
*A61B 18/18* (2006.01)
*A61B 18/00* (2006.01)

(52) U.S. Cl.
CPC .......... *A61B 18/1815* (2013.01); *A61B 18/18* (2013.01); *A61B 2018/00017* (2013.01);
(Continued)

(58) Field of Classification Search
CPC ................ A61B 18/18; A61B 18/1815; A61B 2018/1823; A61B 2018/183;
(Continued)

(56) References Cited

U.S. PATENT DOCUMENTS 3,800,552 A 4/1974 Sollami
3,838,242 A 9/1974 Goucher
(Continued)

FOREIGN PATENT DOCUMENTS

AU 2015/202149 5/2015
CN 2579361 10/2003
(Continued)

OTHER PUBLICATIONS

Brace Christopher et al. "Analysis and experimental validation of a triaxial antenna for microwave tumor ablation" IEEE MTTS Int Microw Symp. Jun. 3, 2004(6-11) 1437-1440.
(Continued)

*Primary Examiner* — Ronald Hupczey, Jr.
*Assistant Examiner* — Bradford C. Blaise
(74) *Attorney, Agent, or Firm* — Casimir Jones, SC; Robert A. Goetz

(57) ABSTRACT

Provided herein are devices, systems, and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, devices, systems, and methods are provided for delivering energy to difficult to access tissue regions (e.g. central or peripheral lung tissues), and/or reducing the amount of undesired heat given off during energy delivery.

20 Claims, 7 Drawing Sheets

Related U.S. Application Data

(60) Provisional application No. 62/246,431, filed on Oct. 26, 2015.

(52) U.S. Cl.
CPC ............. *A61B 2018/00023* (2013.01); *A61B 2018/00541* (2013.01); *A61B 2018/00577* (2013.01); *A61B 2018/183* (2013.01); *A61B 2018/1823* (2013.01); *A61B 2018/1861* (2013.01); *A61B 2018/1892* (2013.01)

(58) Field of Classification Search
CPC .... A61B 2018/1861; A61B 2018/1892; A61B 2018/00577
See application file for complete search history.

(56) References Cited

U.S. PATENT DOCUMENTS

| | | | |
|---|---|---|---|
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr |
| 4,586,491 A | 5/1986 | Carpenter |
| 4,589,424 A | 5/1986 | Vaguine |
| 4,601,296 A | 7/1986 | Yerushalmi et al. |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,800,899 A | 1/1989 | Elliott |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner et al. |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Sterzer |
| 5,129,396 A | 7/1992 | Rosen |
| 5,150,717 A | 9/1992 | Rosen |
| 5,167,619 A | 12/1992 | Wuchinich |
| 5,211,625 A | 5/1993 | Sakurai |
| 5,213,561 A | 5/1993 | Weinstein et al. |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Milder |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,364,392 A | 11/1994 | Warner |
| 5,366,490 A | 11/1994 | Edwards |
| 5,369,251 A | 11/1994 | King |
| 5,370,678 A | 12/1994 | Edwards |
| 5,405,346 A | 4/1995 | Grundy |
| 5,431,649 A | 7/1995 | Mulier |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell |
| 5,559,295 A | 9/1996 | Sheryll |
| 5,575,794 A | 11/1996 | Walus |
| 5,578,029 A | 11/1996 | Trelles |
| 5,591,227 A | 1/1997 | Dinh |
| 5,597,146 A | 1/1997 | Putman |
| 5,599,295 A | 2/1997 | Rosen |
| 5,599,352 A | 2/1997 | Dinh |
| 5,603,697 A | 2/1997 | Grundy |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt |
| 5,921,935 A | 7/1999 | Hickey |
| 5,957,969 A | 9/1999 | Warner |
| 5,963,082 A | 10/1999 | Dick |
| 5,995,875 A | 11/1999 | Blewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |
| 6,165,163 A | 12/2000 | Chien |
| 6,174,307 B1 | 1/2001 | Daniel et al. |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly |
| 6,223,085 B1 | 4/2001 | Dann |
| 6,230,060 B1 | 5/2001 | Mawhinney |
| 6,235,022 B1 | 5/2001 | Hallock |
| 6,241,725 B1 | 6/2001 | Cosman |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |

(56) References Cited

U.S. PATENT DOCUMENTS

| | | |
|---|---|---|
| 6,273,884 B1 | 8/2001 | Altshuler |
| 6,273,885 B1 | 8/2001 | Koop |
| 6,273,886 B1 | 8/2001 | Edwards |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,312,427 B1 | 11/2001 | Berube |
| 6,325,796 B1 | 12/2001 | Berube |
| 6,347,251 B1 | 2/2002 | Deng |
| 6,355,033 B1 | 3/2002 | Moorman |
| 6,364,876 B1 | 4/2002 | Erb |
| 6,383,182 B1 | 5/2002 | Berube |
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,351 B1 | 10/2002 | Woodruff et al. |
| 6,461,352 B2 | 10/2002 | Morgan |
| 6,471,696 B1 | 10/2002 | Berube |
| 6,500,174 B1 | 12/2002 | Maguire |
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 | 6/2003 | Rittman, III et al. |
| 6,577,903 B1 | 6/2003 | Cronin |
| 6,582,426 B2 | 6/2003 | Moorman |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,673,068 B1 | 1/2004 | Berube |
| 6,683,625 B2 | 1/2004 | Muthusamy |
| 6,694,163 B1 | 2/2004 | Vining |
| 6,699,240 B2 | 3/2004 | Francischelli |
| 6,702,576 B2 | 3/2004 | Fischer |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire et al. |
| 6,875,209 B2 | 4/2005 | Zvuloni et al. |
| 6,878,147 B2 | 4/2005 | Prakash |
| 6,890,968 B2 | 5/2005 | Angeletakis |
| 6,893,436 B2 | 5/2005 | Woodard |
| 6,898,454 B2 | 5/2005 | Atalar |
| D507,649 S | 7/2005 | Padain |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | Van der Weide |
| 7,115,126 B2 | 10/2006 | Berube |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen |
| 7,266,407 B2 | 9/2007 | Li et al. |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 6/2008 | Van der Walt |
| 7,400,929 B2 | 7/2008 | Zelickson et al. |
| 7,402,140 B2 | 7/2008 | Spero |
| 7,410,484 B2 | 8/2008 | Littrup |
| 7,467,015 B2 | 12/2008 | Van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,035,570 B2 | 10/2011 | Prakash |
| 8,059,059 B2 | 11/2011 | Bonn |
| 8,093,500 B2 | 1/2012 | Deborski |
| 8,109,895 B2 | 2/2012 | Williams et al. |
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,357,148 B2 | 1/2013 | Boulais et al. |
| 8,403,924 B2 | 3/2013 | Behnke |
| 8,430,871 B2 | 4/2013 | Brannan |
| 8,454,589 B2 | 6/2013 | Deno |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide et al. |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |

(56) References Cited

U.S. PATENT DOCUMENTS

| | | |
|---|---|---|
| 9,192,438 B2 | 11/2015 | Thiel |
| 9,198,725 B2 | 12/2015 | Willyard |
| 9,220,441 B2 | 12/2015 | Yoo |
| 10,952,792 B2 * | 3/2021 | Thiel .................. A61B 18/1815 |
| 2001/0020166 A1 | 9/2001 | Daly et al. |
| 2001/0039416 A1 | 11/2001 | Moorman et al. |
| 2001/0049524 A1 | 12/2001 | Morgan et al. |
| 2002/0022836 A1 | 2/2002 | Goble |
| 2002/0026187 A1 | 2/2002 | Swanson et al. |
| 2002/0026188 A1 | 2/2002 | Balbierz et al. |
| 2002/0040185 A1 | 4/2002 | Atalar et al. |
| 2002/0072742 A1 | 6/2002 | Schaefer |
| 2002/0087151 A1 | 7/2002 | Mody |
| 2002/0087157 A1 | 7/2002 | Sliwa, Jr. et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash |
| 2003/0120268 A1 | 6/2003 | Bertolero |
| 2003/0130711 A1 | 7/2003 | Pearson et al. |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 7/2004 | Sterzer |
| 2004/0158237 A1 | 8/2004 | Abboud |
| 2004/0186517 A1 | 9/2004 | Hill |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1 | 1/2005 | Turovskiy |
| 2005/0075629 A1 | 4/2005 | Chapelon |
| 2005/0107870 A1 | 5/2005 | Wang |
| 2005/0109900 A1 | 5/2005 | Schilt |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Welde |
| 2005/0245920 A1 | 11/2005 | Vitullo et al. |
| 2006/0064083 A1 | 3/2006 | Khalaj |
| 2006/0079886 A1 | 4/2006 | Orszulak et al. |
| 2006/0094956 A1 | 5/2006 | Vismanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch |
| 2006/0276780 A1 | 12/2006 | Brace |
| 2006/0276781 A1 | 12/2006 | van der Weide et al. |
| 2006/0289528 A1 | 12/2006 | Chiu |
| 2006/0293652 A1 | 12/2006 | van der Weide et al. |
| 2007/0016180 A1 | 1/2007 | Lee et al. |
| 2007/0016181 A1 | 1/2007 | van der Weide et al. |
| 2007/0021741 A1 | 1/2007 | Marwan et al. |
| 2007/0055224 A1 | 3/2007 | Lee et al. |
| 2007/0066972 A1 | 3/2007 | Ormsby |
| 2007/0185554 A1 | 8/2007 | Appling |
| 2007/0203551 A1 | 8/2007 | Cronin |
| 2007/0208389 A1 | 9/2007 | Amundson et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn et al. |
| 2009/0281536 A1 | 11/2009 | Beckman et al. |
| 2009/0306644 A1 | 12/2009 | Mayse et al. |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn et al. |
| 2011/0098696 A1 | 4/2011 | Brannan |
| 2011/0118723 A1 | 5/2011 | Turner |
| 2011/0118725 A1 | 5/2011 | Mayse |
| 2011/0213352 A1 | 9/2011 | Lee |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |
| 2012/0209257 A1 | 8/2012 | Weide et al. |
| 2012/0209261 A1 | 8/2012 | Mayse |
| 2012/0209296 A1 | 8/2012 | Mayse |
| 2012/0232544 A1 | 9/2012 | Willyard |
| 2012/0232549 A1 | 9/2012 | Willyard |
| 2012/0310228 A1 | 12/2012 | Bonn |
| 2012/0316551 A1 | 12/2012 | van der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham et al. |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1 | 10/2013 | Mallya et al. |
| 2013/0281851 A1 | 10/2013 | Carr |
| 2013/0306543 A1 | 11/2013 | Beisser |
| 2013/0338530 A1 | 12/2013 | Kassab |
| 2014/0005706 A1 | 1/2014 | Gelfand |
| 2014/0046174 A1 | 2/2014 | Ladtkow |
| 2014/0046176 A1 | 2/2014 | Ladtkow |
| 2014/0152656 A1 | 6/2014 | Yoo |
| 2014/0163664 A1 | 6/2014 | Goldsmith et al. |

(56) References Cited

U.S. PATENT DOCUMENTS

| | | |
|---|---|---|
| 2014/0276033 A1 | 9/2014 | Brannan |
| 2014/0276200 A1 | 9/2014 | Brannan |
| 2015/0148792 A1 | 5/2015 | Kim |
| 2015/0150628 A1 | 6/2015 | Buysse |
| 2015/0164587 A1 | 6/2015 | Bonn et al. |
| 2015/0190193 A1 | 7/2015 | Mayse |
| 2015/0250540 A1 | 9/2015 | Behdad |
| 2015/0351839 A1 | 12/2015 | Brannan |
| 2015/0374438 A1 | 12/2015 | van der Weide |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1723922 A | 11/2006 |
| EP | 2098184 | 9/2009 |
| EP | 2295000 | 3/2011 |
| EP | 2316370 | 5/2011 |
| EP | 1659969 | 10/2012 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| JP | 2012-250035 | 12/2012 |
| JP | 2014/514071 | 6/2014 |
| JP | 2015/503963 | 5/2015 |
| JP | 2015-514504 | 5/2015 |
| WO | WO 92/04934 | 4/1992 |
| WO | WO 93/09845 | 5/1993 |
| WO | WO 95/004385 | 9/1995 |
| WO | WO 97/48449 | 12/1997 |
| WO | WO 99/56643 | 11/1999 |
| WO | 2000/057811 | 10/2000 |
| WO | WO 00/57811 | 10/2000 |
| WO | WO 01/70114 | 9/2001 |
| WO | WO 03/039385 | 5/2003 |
| WO | 2003/086190 | 10/2003 |
| WO | WO 03/086498 | 10/2003 |
| WO | WO 03/088806 | 10/2003 |
| WO | WO 03/088858 | 10/2003 |
| WO | WO 2004/004586 | 1/2004 |
| WO | WO 04026122 | 1/2004 |
| WO | WO 04/033039 | 4/2004 |
| WO | WO 2004/084748 | 10/2004 |
| WO | WO 04/112628 | 12/2004 |
| WO | WO 05/011049 | 2/2005 |
| WO | WO 05/034783 | 4/2005 |
| WO | WO 05/110265 | 11/2005 |
| WO | 2006/002843 | 1/2006 |
| WO | 2006/004585 | 1/2006 |
| WO | WO 06/002943 | 1/2006 |
| WO | WO 06/005579 | 1/2006 |
| WO | WO 06/008481 | 1/2006 |
| WO | WO 2006/084676 | 8/2006 |
| WO | 2006/122149 | 11/2006 |
| WO | 2006/127847 | 11/2006 |
| WO | WO 2006/12149 | 11/2006 |
| WO | 2007/076924 | 7/2007 |
| WO | WO 2007/112103 | 10/2007 |
| WO | WO 2008/008545 | 1/2008 |
| WO | WO 2008/044013 | 4/2008 |
| WO | WO 08/142686 | 11/2008 |
| WO | 2010/067360 | 6/2010 |
| WO | WO 11/008903 | 1/2011 |
| WO | 2011/017168 | 2/2011 |
| WO | WO 2011/140087 | 11/2011 |
| WO | 2013/158392 | 10/2013 |
| WO | 2013/173481 | 11/2013 |
| WO | WO 2013/173481 | 11/2013 |

OTHER PUBLICATIONS

Brace Christopher et al. "Microwave Ablation with a Triaxial Antenna: Results in ex vivo Bovine Liver" IEEE Transations on Microwave Theory and Techniques vol. 53 No. Jan. 1, 2005.

English translation of a Decision of Refusal from related Japanese Patent Application No. 2013-509179 dated Jun. 30, 2015.

European Search Report dated Mar. 3, 2009 EP Patent Application No. 06 802 385.2.

Golio "The RF and microwave handbook" Edition: 2. Published by CRC Press 2001 ISBN 0849338592X 97808493859626.

Head Hayden W. et al. "Thermal Ablation for Hepatocellular Carcinoma" Gastroenterology 2004:127:S167-S178.

International Search Report PCT/US06/031644 dated Aug. 17, 2007.

International Search Report PCT/US06/032811 dated Jan. 25, 2007.

International Search Report PCT/US2005/014534 dated Nov. 29, 2005.

International Search Report PCT/US2006/017981 dated Sep. 7, 2006.

International Search Report PCT/US2006/028821 dated Mar. 21, 2007.

International Search Report PCT/US2006/033341 dated Aug. 17, 2007.

SEKI Toshihito et al. "Ultrasonically Guided Percutaneous Microwave Coagulation Therapy for Small Hepatocellular Carcinoma" Cancer Aug. 1, 1994 vol. 74 No. 3 pp. 817-825.

International Search Report PCT/US16/5888 dated Feb. 15, 2017.

International Search Report PCT/US2016/058890 dated Jan. 19, 2017.

"Carbon dioxide." Carbon dioxide—New World Encyclopedia. Web. www.newworldencyclopedia.org/entry/Carbon_dioxide.

European Search Report, EP Patent Application No. 11778168, dated Oct. 2, 2013.

International Preliminary Report, PCT/US2007/007464, dated Sep. 30, 2008.

International Preliminary Report on Patentability, PCT/US2012/071310, dated Aug. 19, 2014.

International Preliminary Report on Patentability, PCT/US2011/035000, dated Nov. 6, 2012.

International Preliminary Report on Patentability, PCT/US2010/043558, dated Jan. 31, 2012.

Guy, Aw (1971) IEEE Trans. Microwave Theory Tech. 19 pp. 205-214.

European Search Report, EP Patent Application No. 12860249.7, dated Sep. 15, 2015.

European Search Report, EP Patent Application No. 10806929.5, dated Feb. 21, 2013.

European Search Report, EP Patent Application No. 07810483, dated Mar. 22, 2013.

International Search Report, PCT/US2007/016082, dated Jul. 21, 2008.

(56) References Cited

OTHER PUBLICATIONS

International Search Report, PCT/US2011/035000, dated Jan. 6, 2012.
International Search Report, PCT/US2012/071310, dated Feb. 25, 2013.
International Preliminary Report on Patentability, PCT/US2007/016082, dated Jan. 14, 2009.
Supplementary European Search Report dated May 20, 2019, EP Patent Application No. 16860697.8, 8 pages.
European Search Report dated Mar. 9, 2015, EP Patent Application No. 14189493.1.
International Preliminary Report on Patentability re: PCT/US2007/007408 dated Sep. 30, 2008.
International Preliminary Report on Patentability re: PCT/US2016/058888 dated Dec. 11, 2017.
International Preliminary Report on Patentability re: PCT/US2016/058890 dated May 11, 2018.
International Search Report & Written Opinion, International Patent Application No. PCT/US2017/027424, dated Oct. 9, 2017.
European Search Report, EP Patent Application No. 17168163,8, dated Sep. 13, 2017.

\* cited by examiner

ENERGY DELIVERY SYSTEMS AND USES THEREOF

CROSS REFERENCE TO RELATED APPLICATIONS

This application is a continuation of U.S. patent application Ser. No. 15/335,155, filed Oct. 26, 2016 (now U.S. Pat. No. 10,952,792), which claims priority to and the benefit of U.S. Provisional Application No. 62/246,431, filed Oct. 26, 2015, the contents of which are hereby incorporated by reference in their entireties.

FIELD OF THE INVENTION

Provided herein are devices, systems, and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, devices, systems, and methods are provided for delivering energy to difficult to access tissue regions (e.g. central or peripheral lung tissues), and/or reducing the amount of undesired heat given off during energy delivery.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices are limited, by size and flexibility, as to the body regions to which they are capable of delivering energy. For example, in the lungs, the air paths of the bronchial tree get progressively narrower as they branch with increasing depth into the periphery of the lungs. Accurate placement of energy delivery devices to such difficult to reach regions is not feasible with current devices. Further, existing microwave systems are incapable of delivery sufficient microwave energy to distant ablation target regions without overheating and burning tissue along the pathway. Improved systems and devices for delivering energy to difficult to reach tissue regions are needed.

SUMMARY OF THE INVENTION

Provided herein are devices, systems, and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, devices, systems, and methods are provided for delivering energy to difficult to access tissue regions (e.g. central and peripheral lung tissues), and/or reducing the amount of undesired heat given off during energy delivery. In some embodiments, systems, devices, and methods are provided for reducing heat release along energy transmission lines.

In some embodiments, provided herein are systems, devices, and methods that employ components for the delivery of energy to a tissue region (e.g., tumor, lumen, organ, etc.). In some embodiments, the system comprises an energy delivery device and one or more of: a processor, a power supply, a components for directing, controlling and delivering power (e.g., a power splitter), an imaging system, a tuning system, a temperature adjustment system, and a device placement system.

There are a number of significant challenges to delivering ablative amounts of energy to distant or hard-to-reach locations within a body (e.g., central and peripheral lung tissues). For example, for endobronchial or transbronchial therapies, such techniques may require long, flexible delivery pathways and small diameter devices. These factors complicate the delivery of sufficiently high amounts of energy to the target tissue. Increasing energy delivery along such a path creates significant heating and poses challenges to the materials used. Heating can burn tissue along the pathway causing undesired or unacceptable damage. Provided herein are devices, system, and methods that overcome these challenges and balance the factors needed to achieve successful tissue ablation with long, flexible, small diameter devices able to reach remote areas of the body (e.g., endobronchially and transbronchially).

In some embodiments, the devices, systems, and methods employ a co-axial or triaxial microwave energy delivery device having coolant flowed through a first channel of the device from its proximal end to its distal end and wherein the coolant is reversed at the distal end and flows back through the device distal to proximal through a different channel. In some embodiments, the first channel is provided in a hollow center of an inner conductor and the return channel is provided between the inner and outer conductors.

For example, in some embodiments, provided herein is an energy delivery device for delivering microwave energy to a distant region of a body, comprising one or more or each of: a) a proximal end connectable or connected, directly or indirectly, to a microwave energy generator and/or a coolant source; b) a distal end configured to generate ablative energy in a defined region surrounding the distal end so as to ablate a desired tissue region; c) an inner conductor (e.g., a hollow inner conductor; d) a spacer surrounding a portion of the inner conductor (e.g., a monofilament tube spiraled around the inner conductor); e) a non-conductive core (e.g., dielectric core) surrounding the spacer, whereby an air gap is formed between the core and the inner conductor in regions not occupied by the spacer; f) an outer conductor surrounding the core; and a coolant flow exchanger at the distal end configured to receive coolant from one source (e.g., a hollow inner conductor) and return coolant to the air gap.

In some embodiments, the energy delivery device is sufficiently long to extend from outside of the body to a target region inside of the body. Thus, in some embodiments, the energy delivery device is at least 20 centimeter longs (e.g., at least 30, 40, 50, 60, 70, 80, 90, 100, 110, 120, 130, 140, 150, 160, 170, 180, 190, 200, etc. cm longs or ranges therein between).

In some embodiments, the energy delivery device further comprises a non-conductive jacket surrounding the outer conductor. In some embodiments, the energy delivery device further comprises a conductive sheath surrounding the non-conductive jacket, the conductive sheath forming a triaxial antenna with the outer conductor and the inner conductor.

In some embodiments, the energy delivery device further comprises a trocar or conical or other tissue-penetrating tip at its distal end. In some embodiments, the tip is conductive. In some embodiments, the inner conductor is not electrically connected to the tip. In some embodiments, the inner conductor is capacitively coupled to the tip.

In some embodiments, the coolant flow exchanger comprise a cap having an open proximal end forming an opening within the cap and a closed distal end. In some embodiments, the inner conductor is inserted into the opening in the cap. In some embodiments, the opening in the cap comprises one or more channels that return coolant from the inner conductor out of the open proximal end of the cap and into the air gap.

In some embodiments, the device has an outer diameter sized for endobronchial delivery of microwave energy to a central or peripheral lung nodule (e.g., less than 3 mm, 2.8 mm, 2.5 mm, 2.3 mm, 2.1 mm, 2 mm, 1.9 mm, 1.8 mm, 1.7 mm, 1.6 mm, 1.5 mm, 1.4 mm, etc.).

Further provided herein are systems comprising such an energy delivery device and one or more other components. Such systems may further comprise a delivery system for delivering the energy delivery device from outside of the body to the target region inside of the body (e.g., from a subject's mouth endobronchially or transbronchially to a central or peripheral lung region). In some embodiments, the system comprises a delivery tube. In some embodiments, the delivery tube is conductive. In some such embodiments, the delivery tube provides an outermost conductor that forms a triaxial antenna with the outer and inner conductors of the energy delivery device. In some embodiments, the delivery tube provide an outer conductor and the energy delivery device includes only an inner conductor, the delivery device completing the coaxial antenna. In some embodiments, the system comprises a generator (e.g., a microwave generator). In some embodiments, the system comprises a coolant supply (e.g., a supply of pressurized gas such as $CO_2$). In some embodiments, the coolant supply delivers coolant through the inner conductor or other passageway at from zero to 1000 psi (e.g., 700 psi). In some embodiments, the system comprises a control computer that controls any desired system components, including timing and amount of energy and/or coolant delivery. In some embodiments, the system comprises an imaging device. In some embodiments, the system comprises an energy and coolant interface to link the energy delivery device to power and coolant supplies. In some embodiments, the interface comprises: a) a gas connector for connecting to a coolant source; b) a power connector for connecting to an electrical source; and c) an ablative power connector for connecting to a microwave generator.

Further provided herein are methods of using the energy delivery devices or associated systems. In some embodiments, provided herein are methods of ablating tissue comprising: positioning the distal end of an energy delivery device near a target tissue and applying ablative energy from the device. In some embodiments, the tissue is in a lung. In some embodiments, the energy delivery device is positioned endobronchially or transbronchially. In some embodiments, the target tissue is a central or peripheral lung nodule. In some embodiments, the systems, devices, and methods access lung nodules, tumors, and/or lesions on central or peripheral lung tissue (e.g. without entry into the lung by piercing the lung tissue). In some embodiments, the systems, devices, and methods provide access to lung nodules, tumors, and/or lesions on central or peripheral lung tissue through the trachea and/or bronchial tree (e.g. primary, secondary, and tertiary bronchia, and bronchioles). In some embodiments, the systems, devices, and methods deliver energy (e.g. microwave energy) through the bronchial tree to the central or peripheral lung without tissue damage (e.g. without significantly damaging the tissue along the path).

The systems are not limited by the nature of the coolant material employed. Coolants included, but are not limited to, liquids and gases. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, the coolant fluid also serves as the dielectric material. In some embodiments, the coolant is a gas compressed at or near its critical point. In some embodiments, cooling occurs, at least in part, by changing concentrations of coolant, pressure, volume, or temperature. For example, cooling can be achieved via gas coolants using the Joule-Thompson effect. In some embodiments, the cooling is provided by a chemical reaction. The devices are not limited to a particular type of temperature reducing chemical reaction. In some embodiments, the temperature reducing chemical reaction is an endothermic reaction. In some embodiments, the coolant is a super-cooled gas. In some embodiments, cooling is controlled by a pressure control system. In some embodiments, cooling of a coolant employs a thermoelectric chiller (e.g., Peltier cooler, heat-exchanger, etc.).

In some embodiments, the energy delivery devices prevent undesired heating and/or maintain desired energy delivery properties through adjusting the amount of energy emitted from the device (e.g., adjusting the energy wavelength resonating from the device) as temperatures increase. The devices are not limited to a particular method of adjusting the amount of energy emitted from the device. In some embodiments, the devices are configured such that as the device reaches a certain threshold temperature or as the device heats over a range, the energy wavelength resonating from the device is adjusted. The devices are not limited to a particular method for adjusting energy wavelength resonating from the device. In some embodiments, the energy delivery devices prevent undesired heating and/or maintain desired energy delivery properties through adjusting the energy delivery program without adjusting (e.g., lowering) the energy wavelength. In some embodiments, pulsed programs deliver bursts of energy to the treatment site (e.g. bursts of energy sufficient to perform the desired task (e.g.

ablation)) without inducing undesired heating along the transmission path. In some embodiments, pulsed programs reduce heat along the transmission pathway when compared to continuous delivery programs. In some embodiments, different patterns of pulse programs effectively balance the potentially conflicting desires of large amounts of energy delivered to the treatment site and reduced heat along the delivery path. In some embodiments, different pulse patterns (e.g. length of time delivering energy, length of time between energy pulses) and different energy levels (e.g. energy wavelengths) are utilized to optimize energy-delivery and path-heating.

In some embodiments, the energy delivery devices comprise a triaxial microwave probe with optimized tuning capabilities to reduce reflective heat loss (see, e.g., U.S. Pat. No. 7,101,369; see, also, U.S. patent application Ser. Nos. 10/834,802, 11/236,985, 11/237,136, 11,237,430, 11/440, 331, 11/452,637, 11/502,783, 11/514,628; and International Patent Application No. PCT/US05/14534; herein incorporated by reference in its entirety). In some embodiments, the energy delivery devices emit energy through a coaxial transmission line (e.g., coaxial cable) having air or other gases as a dielectric core (see, e.g., U.S. patent application Ser. No. 11/236,985; herein incorporated by reference in its entirety).

The control systems are not limited to a particular type of controller or processor. In some embodiments, the processor is designed to, for example, receive information from components of the system (e.g., temperature monitoring system, energy delivery device, tissue impedance monitoring component, etc.), display such information to a user, and manipulate (e.g., control) other components of the system. In some embodiments, the processor is configured to operate within a system comprising an energy delivery device, a power supply, a means of directing, controlling and delivering power (e.g., a power splitter), an imaging system, a tuning system, and/or a temperature adjustment system.

The systems, devices, and methods are not limited to a particular type of power supply. In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the power supply utilizes a power splitter to permit delivery of energy to two or more energy delivery devices. In some embodiments, the power supply is configured to operate within a system comprising a power splitter, a processor, an energy delivery device, an imaging system, a tuning system, and/or a temperature adjustment system.

The systems, devices, and methods are not limited to a particular type of imaging system. In some embodiments, the imaging system utilizes imaging devices (e.g., endoscopic devices, stereotactic computer assisted neurosurgical navigation devices, thermal sensor positioning systems, motion rate sensors, steering wire systems, intraprocedural ultrasound, fluoroscopy, computerized tomography magnetic resonance imaging, nuclear medicine imaging devices triangulation imaging, interstitial ultrasound, microwave imaging, acoustic tomography, dual energy imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention. In some embodiments, the imaging system is configured to provide location information of particular components of the energy delivery system (e.g., location of the energy delivery device). In some embodiments, the imaging system is configured to operate within a system comprising a processor, an energy delivery device, a power supply, a tuning system, and/or a temperature adjustment system. In some embodiments, the imaging system is located within the energy delivery device. In some embodiments, the imaging system provides qualitative information about the ablation zone properties (e.g., the diameter, the length, the cross-sectional area, the volume). The imaging system is not limited to a particular technique for providing qualitative information. In some embodiments, techniques used to provide qualitative information include, but are not limited to, time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices. In some embodiments, the interstitial device provides a signal and/or detection for imaging (e.g., electro-acoustic imaging, electromagnetic imaging, electrical impedance tomography).

The systems, devices, and methods are not limited to a particular tuning system. In some embodiments, the tuning system is configured to permit adjustment of variables (e.g., amount of energy delivered, frequency of energy delivered, energy delivered to one or more of a plurality of energy devices that are provided in the system, amount of or type of coolant provided, etc.) within the energy delivery system. In some embodiments, the tuning system comprises a sensor that provides feedback to the user or to a processor that monitors the function of an energy delivery device continuously or at time points. In some embodiments, reflected energy is monitored to assess energy delivery. The sensor may record and/or report back any number of properties, including, but not limited to, heat (e.g., temperature) at one or more positions of a component of the system, heat at the tissue, property of the tissue, qualitative information of the region, and the like. The sensor may be in the form of an imaging device such as CT, ultrasound, magnetic resonance imaging, fluoroscopy, nuclear medicine imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.). In some embodiments, the tuning system is configured to operate within a system comprising a processor, an energy delivery device, a power supply, an imaging, and/or a temperature adjustment system. In some embodiments, the imaging or other control components provide feedback to the ablation device so that the power output (or other control parameter) can be adjusted to provide an optimum tissue response.

The systems, devices, and methods are not limited to a particular temperature adjustment system. In some embodiments, the temperature adjustment systems are designed to reduce unwanted heat of various components of the system (e.g., energy delivery devices) during medical procedures (e.g., tissue ablation) or keep the target tissue within a certain temperature range. In some embodiments, the temperature adjustment systems are configured to operate within a system comprising a processor, an energy delivery device, a power supply, components for directing, controlling and delivering power (e.g., a power splitter), a tuning system, and/or an imaging system.

In some embodiments, the systems further comprise temperature monitoring or reflected power monitoring systems for monitoring the temperature or reflected power of various components of the system (e.g., energy delivery devices) and/or a tissue region. In some embodiments, the monitoring systems are designed to alter (e.g., prevent, reduce) the delivery of energy to a particular tissue region if, for example, the temperature or amount of reflected energy, exceeds a predetermined value. In some embodiments, the temperature monitoring systems are designed to alter (e.g., increase, reduce, sustain) the delivery of energy to a particular tissue region so as to maintain the tissue or energy delivery device at a preferred temperature or within a preferred temperature range.

In some embodiments, the systems further comprise an identification or tracking system configured, for example, to prevent the use of previously used components (e.g., non-sterile energy delivery devices), to identify the nature of a component of the system so the other components of the system may be appropriately adjusted for compatibility or optimized function. In some embodiments, the system reads a bar code or other information-conveying element associated with a component of the systems of the invention. In some embodiments, the connections between components of the system are altered (e.g., broken) following use so as to prevent additional uses. The present invention is not limited by the type of components used in the systems or the uses employed. Indeed, the devices may be configured in any desired manner. Likewise, the systems and devices may be used in any application where energy is to be delivered. Such uses include any and all medical, veterinary, and research applications.

The systems, devices, and methods are not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, lung (e.g. central or peripheral lung), abdomen, and pelvis. In some embodiments, the systems are configured for guided delivery, for example, by computerized tomography, ultrasound, magnetic resonance imaging, fluoroscopy, and the like.

The systems, devices, and methods may be used in conjunction with other systems, device, and methods. For example, the systems, devices, and methods of the present invention may be used with other ablation devices, other medical devices, diagnostic methods and reagents, imaging methods and reagents, device placement systems, and therapeutic methods and agents. Use may be concurrent or may occur before or after another intervention.

Additionally, integrated ablation and imaging systems are provided that feature feedback to a user and permit communication between various system components. System parameters may be adjusted during the ablation to optimize energy delivery. In addition, the user is able to more accurately determine when the procedure is successfully completed, reducing the likelihood of unsuccessful treatments and/or treatment related complications.

In some embodiments, the present invention provides devices, systems, and methods for placing energy delivery devices in difficult to reach structures, tissue regions, and/or organs (e.g. a branched structure (e.g. human lungs). Accordingly, in some embodiments, the present invention provides a multiple-catheter system or device comprising: a primary catheter, which comprises an inner lumen (the primary lumen); a channel catheter, or sheath, which comprises an inner lumen (channel lumen), wherein the channel catheter is configured to fit within the primary lumen; and one or more insertable tools (e.g. steerable navigation catheter, therapeutic tools (e.g. energy delivery device, biopsy forceps, needles, etc.), etc.), wherein one or more insertable tools are configured to fit within the channel lumen. In some embodiments, the present invention provides a method for accessing difficult to access tissue regions (e.g. highly branched tissue, e.g. periphery of the lungs) comprising: providing a steerable navigation catheter within the channel lumen of a channel catheter, wherein the channel catheter is within the primary lumen of a primary catheter. In some embodiments, a steerable navigation catheter comprises: i) a steerable tip which allows manipulation of its position within a patient, organ, lumen, and/or tissue by a clinician or operator, and ii) a position sensor, which allows tracking of the steerable navigation catheter through a patient, organ, lumen, and/or tissue. In some embodiments, a steerable tip of a steerable navigation catheter functions by pointing tip of the catheter in the desired direction of motion. In some embodiments, manual or automated movement of the catheter results in movement directed in the direction of the tip. In some embodiments, a primary catheter, channel catheter, and steerable navigation catheter are inserted into a tissue region (e.g. bronchi) within a patient, and the primary catheter (e.g. bronchoscope) is inserted as far into the tissue region as the size of the available space (e.g. lumen (e.g. lumen of the brochia)) and the size of the primary catheter (e.g. bronchoscope) will allow. In some embodiments, the primary catheter, channel catheter and steerable navigation catheter are moved through the patient, organ, lumen, and/or tissue via the steerable tip of the steerable navigation catheter and/or steering mechanisms within the primary catheter. In some embodiments, the channel catheter and steerable navigation catheter are extended beyond the end of the primary catheter to access smaller, deeper, and/or more difficult to access tissue regions (e.g. central or peripheral bronchi, bronchioles, etc.). In some embodiments, the channel catheter and steerable navigation catheter are moved through the patient, organ, lumen, and/or tissue via the steerable tip of the steerable navigation catheter. In some embodiments, the position of the channel catheter and steerable navigation catheter are monitored via the position sensor of the steerable navigation catheter. In some embodiments, the distal ends of the channel catheter and steerable navigation catheter are placed at the target site (e.g. treatment site) in the patient, organ, lumen, and/or tissue (e.g. central or peripheral bronchi of the lung, central or peripheral lung nodule, etc.). In some embodiments, upon proper placement of the distal ends of the channel catheter and steerable navigation catheter at the target site (e.g. treatment site), the channel catheter (e.g. distal end of the channel catheter) is secured into position. In some embodiments, the distal end of the channel catheter is secured in proper place using any suitable stabilization mechanism (e.g. screws, clips, wings, etc.), as is understood in the art. In some embodiments, upon proper placement of the distal ends of the channel catheter and steerable navigation catheter at the target site (e.g. treatment site), the steerable navigation catheter is withdrawn through the channel catheter and out the proximal end of the channel catheter. In some embodiments, withdrawing the steerable catheter from the proximal end of the channel catheter leaves the channel catheter in place as a channel for accessing the target site (e.g. treatment site) with any suitable insertable tools (e.g. therapeutic tools (e.g. energy delivery device, biopsy device, etc.), etc.). In some embodiments, a properly positioned and secured channel catheter with the steerable navigation catheter removed comprises a guide channel for accessing the target site (e.g. central or peripheral bronchi of the lung) with insertable tools (e.g. energy delivery device, biopsy device, etc.) from outside a subject's body. In some embodiments, one or more insertable tools (e.g. therapeutic tools (e.g. energy delivery device, biopsy device, etc.) are inserted through the vacant channel catheter (e.g. guide channel) and the distal tip of the insertable tool is placed at the target site (e.g. treatment site). In some embodiments, an energy delivery device (e.g. microwave ablation device) is inserted through the vacant channel catheter (e.g. guide channel) and the distal tip of the energy delivery device is placed at the target site (e.g. treatment site). In some embodiments, energy (e.g. microwave energy) is delivered through the channel catheter via the inserted energy delivery device to deliver energy to the target site (e.g. to ablate tissue at the target site).

In some embodiments, the present invention provides a method for steering a catheter through a branched structure to a target location, comprising: (a) providing a steerable navigation catheter, wherein the steerable navigation catheter comprises a position sensor element located near a distal tip of the catheter, the position sensor element being part of a system measuring a position and a pointing direction of the tip of the catheter relative to a three-dimensional frame of reference; (b) designating the target location relative to the three-dimensional frame of reference; (c) advancing the catheter into the branched structure; and (d) displaying a representation of at least one parameter defined by a geometrical relation between the pointing direction of the tip of the catheter and a direction from the tip of the catheter towards the target location. In some embodiments, the steerable navigation catheter resides in the lumen of a channel catheter. In some embodiments, the steerable navigation catheter directs the movement of the channel catheter by the above mechanism. In some embodiments, the steerable navigation catheter and channel catheter reside in the lumen of a primary catheter (e.g. bronchoscope). In some embodiments, the steerable navigation catheter directs the movement of the channel catheter and primary catheter by the above mechanism. In some embodiments, a primary catheter has a separate direction control (steering) mechanism from the steerable navigation catheter.

In some embodiments, a representation of at least one parameter defined by a geometrical relation between (i) the pointing direction of the tip of the steerable navigation catheter and (ii) a direction from the tip of the steerable navigation catheter towards the target location is displayed (e.g. to provide users with information regarding the position and/or direction of the steerable navigation catheter). In some embodiments, the at least one parameter includes an angular deviation between the pointing direction of the tip of the steerable navigation catheter and a direction from the tip of the steerable navigation catheter towards the target location. In some embodiments, the at least one parameter includes a direction of deflection required to bring the pointing direction of the steerable navigation catheter into alignment with the target location. In some embodiments, the representation of at least one parameter is displayed in the context of a representation of a view taken along the pointing direction of the tip of the steerable navigation catheter. In some embodiments, the position sensor element is part of a six-degrees-of-freedom position measuring system measuring the position and attitude of the tip of the steerable navigation catheter in three translational and three rotational degrees of freedom. In some embodiments, the steerable navigation catheter is further provided with a multi-directional steering mechanism configured for selectively deflecting a distal portion of the catheter in any one of at least three different directions. In some embodiments, the steering mechanism is controlled by a user via a control device at the proximal end of the steerable navigation catheter. In some embodiments, the steering mechanism is controlled by a user via a remote control device. In some embodiments, a path traveled by the tip of the steerable navigation catheter is monitored by use of the position sensor element and a representation of the path traveled is displayed together with a current position of the tip, the representation being projected as viewed from at least one direction non-parallel to the pointing direction of the tip.

In some embodiments, the target location (e.g. treatment location (e.g. tumor)) is designated by: (a) designating a target location by use of computerized tomography data of a subject; and (b) registering the computerized tomography data with the three-dimensional frame of reference. In some embodiments, other mapping data (e.g. MM, x-ray, PET, etc.) is substituted for computerized tomography data in any embodiments of the present invention described herein. In some embodiments, the registering is performed by: (a) providing the steerable catheter with a camera; (b) generating a camera view of each of at least three distinctive features within the subject; (c) generating from the computerized tomography data a simulated view of each of the at least three distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography data and the three-dimensional frame of reference. In some embodiments, an intended route through a subject (e.g. through a branched structure (e.g. a lung structure (e.g. bronchi)) within a subject) to a target location is designated by use of the computerized tomography data and a representation of the intended route is displayed together with a current position of the tip, the representation being projected as viewed from at least one direction non-parallel to the pointing direction of the tip. In some embodiments: (a) a current position of the position sensor element is detected; (b) a virtual endoscopy image is generated from the computerized tomography data corresponding to an image that would be viewed by a camera located in predefined spatial relationship and alignment relative to the position sensor element; and (c) displaying the virtual endoscopy image.

In some embodiments, a catheter system of the present invention comprises a steerable navigation catheter and a channel catheter having a lumen extending from a proximal insertion opening to a distal opening; and a guide element configured for insertion through the proximal opening of the sheath to an inserted position extending along the lumen to the distal opening. In some embodiments, a channel catheter is a sheath, through which a steerable navigation catheter (or an energy delivery device) can be inserted and/or withdrawn. In some embodiments, the steerable navigation catheter is used to position the channel catheter such that the distal tips of the steerable navigation catheter and channel catheter are adjacent to the target location (e.g. treatment site (e.g. tumor)). In some embodiments, the channel catheter is locked into proper position at the target location. In some embodiments, the steerable navigation catheter is withdrawn from the channel lumen leaving an open channel extending from the point of insertion into the subject to the target site. In some embodiments, the channel catheter is available for insertion of an insertable tool (e.g. medical tool (e.g. energy delivery device). In some embodiments, the present invention provides a method comprising: (a) guiding a steerable navigation catheter within a channel catheter to a position with the tip adjacent to the target location; and (b) withdrawing the steerable navigation catheter from the channel catheter to leave the channel lumen available for insertion of a medical tool (e.g. energy delivery device).

In some embodiments, a catheter system provides a primary catheter (e.g. flexible endoscope, flexible bronchoscope, etc.) having an operation handle and a primary lumen, a channel catheter deployed within the primary lumen and having a channel lumen, and a steerable navigation catheter deployed within the channel lumen. In some embodiments, the present invention provides a method comprising: inserting the primary catheter, housing the channel catheter and steerable navigation catheter, into a subject, organ, tissue, and/or lumen until the primary catheter reaches its maximum insertion distance (e.g. limited by size from further insertion; (b) locking the steerable navigation catheter within the channel lumen to prevent movement of the steerable navigation catheter relative to the channel catheter; (c) guiding the steerable navigation catheter and channel catheter beyond the distal end of the primary catheter to the target location; (d) locking the channel catheter within the primary lumen to prevent relative movement of the channel catheter relative to the primary catheter and/or operation handle; and (e) unlocking and withdrawing the steerable navigation element from the channel catheter so as to leave the channel in place as a guide for inserting a tool (e.g. energy delivery device) to the target location. In some embodiments, a system or device of the present invention comprises a stabilization and/or anchoring mechanism to hold one or more elements in place when deployed in a subject and/or body region. In some embodiments, a selectively actuatable anchoring mechanism is associated with a portion of the channel catheter. In some embodiments, the selectively actuatable anchoring mechanism includes an inflatable element. In some embodiments, the selectively actuatable anchoring mechanism includes a mechanically deployed element. In some embodiments, a portion of the device is cooled sufficiently to freeze to neighboring tissue, creating a tissue lock (see e.g., U.S. Pat. No. 9,119,649, herein incorporated by reference in its entirety).

In some embodiments, a channel catheter and/or steerable navigation catheter includes an image sensor deployed for generating an image in the pointing direction of the catheter. In some embodiments, the image sensor is configured to be withdrawn with the steerable navigation catheter.

In some embodiments, the present invention provides a method for achieving registration between computerized tomography data (or other mapping data, e.g., MRI, PET, X-ray, etc.) and a three dimensional frame of reference of a position measuring system, the method comprising: (a) providing a catheter with: (i) a position sensor element which operates as part of the position measuring system to allow measurement of a position and a pointing direction of the tip of the catheter relative to the three-dimensional frame of reference, and (ii) an image sensor; (b) generating from the computerized tomography data at least three simulated views of distinctive features within the branched structure; (c) generating at least three camera views of the distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography image and the three-dimensional frame of reference. In some embodiments, designation of a reference point within each of the camera views by the operator is performed by the operator bringing the position sensor element into proximity with the reference point. In some embodiments, designation of a reference point within each simulated view by the operator is performed by: (a) the operator selecting a simulated image reference point within each simulated view; (b) calculating from the simulated image reference point a simulated-viewing-point-to-reference-point vector; and (c) calculating a point of intersection between the simulated-viewing-point-to-reference-point vector and a tissue surface in a numerical model of a portion of the body derived from the computerized tomography data. In some embodiments: (a) at least one location within the computerized tomography data is identified; (b) a position of the at least one location is calculated within the three-dimensional frame of reference; and (c) a representation of the at least one location is displayed together with a representation of a position of the position sensor element. In some embodiments, the at least one location includes a target location (e.g. treatment location (e.g. tumor, bronchi (e.g. central or peripheral bronchi), etc.)) to which a medical tool (e.g. energy delivery device (e.g. microwave ablation device), etc.) is to be directed. In some embodiments, the at least one location is a series of locations defining a planned path along which a medical tool is to be directed. In some embodiments, a method for achieving registration between computerized tomography data and a three dimensional frame of reference of a position measuring system, the method comprising: (a) providing a steerable navigation catheter with: (i) a position sensor element which operates as part of the position measuring system to allow measurement of a position and a pointing direction of the tip of the catheter relative to the three-dimensional frame of reference, and (ii) an image sensor; (b) moving the tip of the catheter along a first branch portion of a branched structure and deriving a plurality of images from the camera, each image being associated with corresponding position data of the position sensor in the three dimensional frame of reference; (c) processing the images and corresponding position data to derive a best-fit of a predefined geometrical model to the first branch portion in the three dimensional frame of reference; (d) repeating steps (b) and (c) for a second branch portion of the branched structure; and (e) correlating the geometrical models of the first and second branch portions with the computerized tomography data to derive a best fit registration between the computerized tomography data and the three dimensional frame of reference. In some embodiments, the processing the images and corresponding position data includes: (a) identifying visible features each of which is present in plural images taken at different positions; (b) for each of the visible features, deriving a camera-to-feature direction in each of a plurality of the images; (c) employing the camera-to-feature directions and corresponding position data to determine a feature position for each visible feature; and (d) deriving a best-fit of the predefined geometrical model to the feature positions. In some embodiments, the predefined geometrical model is a cylinder. In some embodiments: (a) at least one location within the computerized tomography data is identified; (b) a position of the at least one location within the three-dimensional frame of reference is calculated; and (c) a representation of the at least one location is displayed together with a representation of a position of the position sensor element. In some embodiments, the at least one location includes a target location (e.g. treatment location (e.g. tumor (e.g. tumor in the central or peripheral bronchi))) to which a medical tool (e.g. energy delivery device (e.g. microwave ablation device) is to be directed. In some embodiments, the at least one location is a series of locations defining a planned path along which a medical tool is to be directed.

In some embodiments, the present invention provides a steering mechanism for selectively deflecting a distal portion of a steerable navigation catheter in any one of at least two independent directions, the mechanism comprising: (a) at least three elongated tensioning elements extending along the catheter and configured such that tension applied to any one of the tensioning elements causes deflection of a tip of the catheter in a corresponding predefined direction; (b) an actuator displaceable from a first position to a second position; and (c) a selector mechanism configured for selectively mechanically interconnecting a selected at least one of the elongated tensioning elements and the actuator such that displacement of the actuator from the first position to the second position applies tension to the selected at least one of the elongated tensioning elements. In some embodiments, a first state of the selector mechanism mechanically interconnects a single one of the elongated tensioning elements with the actuator such that displacement of the actuator generates deflection of the tip in one of the predefined directions, and a second state of the selector mechanism mechanically interconnects two of the elongated tensioning elements with the actuator such that displacement of the actuator generates deflection of the tip in an intermediate direction between two of the predefined directions. In some embodiments, the at least three tensioning elements includes an even number of the tensioning elements, pairs of the tensioning elements being implemented as a single elongated element extending from the selector mechanism along the catheter to the tip and back along the steerable navigation catheter to the selector mechanism. In some embodiments, the at least three tensioning elements is implemented as four tensioning elements deployed such that each tensioning element, when actuated alone, causes deflection of the tip in a different one of four predefined directions separated substantially by multiples of 90°. In some embodiments, a first state of the selector mechanism mechanically interconnects a single one of the elongated tensioning elements with the actuator such that displacement of the actuator generates deflection of the tip in one of the four predefined directions, and a second state of the selector mechanism mechanically interconnects two of the elongated tensioning elements with the actuator such that displacement of the actuator generates deflection of the tip in one of four intermediate directions each lying between two of the four predefined directions. In some embodiments, the actuator includes a ring which is slidable relative to a handle associated with the catheter, and wherein the selector mechanism includes a slide attached to each of the tensioning elements and slidably deployed within the handle and at least one projection projecting from the ring such that, when the ring is rotated, the at least one projection selectively engages at least one of the slides such that displacement of the ring causes movement of the at least one slide.

BRIEF DESCRIPTION OF THE DRAWINGS

FIG. 3A shows an external view showing proximal opening. FIG. 3B shows a cutaway view. FIG. 3C shows an external view of dimensions.

FIG. 4A shows a completed device. FIG. 4B shows three steps in the manufacture of the device in FIG. 4A.

DETAILED DESCRIPTION

Figure 1:
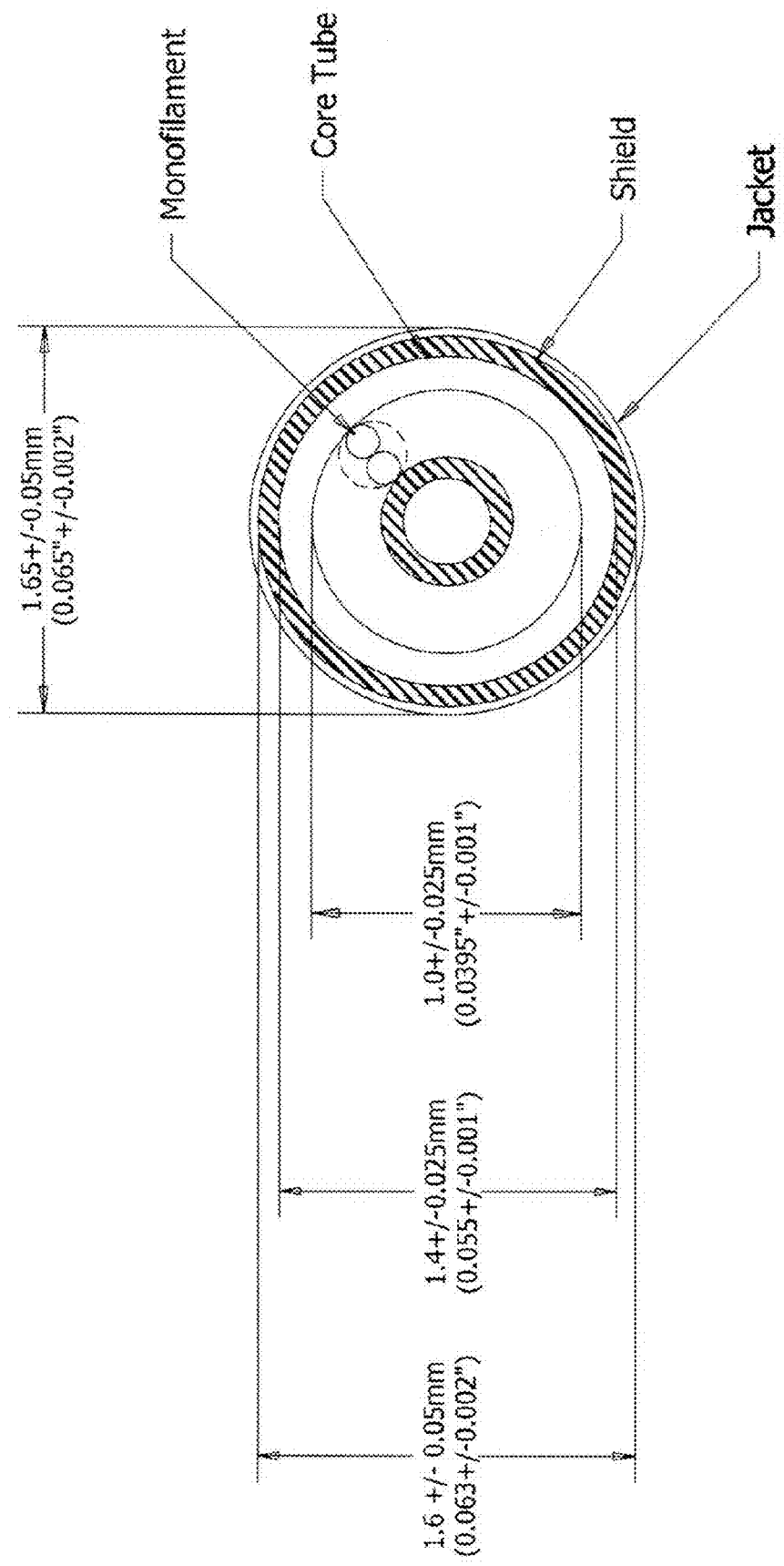
FIG. 1 shows a cross-sectional view of an energy delivery device with coolant channels.

The systems, devices, and methods provided herein provide comprehensive systems, devices and methods for delivering energy (e.g., microwave energy) to tissue for a wide variety of applications, including medical procedures (e.g., tissue ablation (e.g. tumor ablation), resection, cautery, vascular thrombosis, intraluminal ablation of a hollow viscus, cardiac ablation for treatment of arrhythmias, electrosurgery, tissue harvest, cosmetic surgery, intraocular use, etc.). In particular, systems, devices, and methods are provided for treating a difficult to access tissue region (e.g., a central or peripheral lung tumor).

The energy delivery devices described herein may be combined within various system/kit embodiments. For example, systems comprise one or more of a generator, a power distribution system, components for directing, controlling and delivering power (e.g., a power splitter), device placement systems (e.g. multiple catheter system), along with any one or more accessory component (e.g., surgical instruments, software for assisting in procedure, processors, temperature monitoring devices, etc.).

The systems, devices, and methods may be used in any medical procedure (e.g., percutaneous or surgical) involving delivery of energy (e.g., radiofrequency energy, microwave energy, laser, focused ultrasound, etc.) to a tissue region. The systems are not limited to treating a particular type or kind of tissue region (e.g., brain, liver, heart, blood vessels, foot, lung, bone, etc.). For example, the systems of the present invention find use in ablating tumor regions (e.g. lung tumors (e.g. central or peripheral lung tumors)). Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors or central or peripheral lung nodules. In some embodiments, the surgical application comprises the control of hemorrhage (e.g. electrocautery). In some embodiments, the surgical application comprises tissue cutting or removal. In some embodiments, the device is configured for movement and positioning, with minimal damage to the tissue or organism, at any desired location, including but not limited to, the brain, neck, chest, abdomen, pelvis, and extremities. In some embodiments, the device is configured for guided delivery, for example, by computerized tomography, ultrasound, magnetic resonance imaging, fluoroscopy, and the like. In some embodiments, the devices, systems, and methods place energy delivery devices in difficult to reach structures, tissue regions, and/or organs (e.g. a branched structure (e.g. human lungs)).

Exemplary components of the energy delivery systems are described in more detail in the following sections: I. Power Supply; II. Energy delivery devices; III. Processor; IV. Imaging Systems; V. Tuning Systems; VI. Temperature Adjustment Systems; VII. Identification Systems; VIII. Temperature Monitoring Devices; IX. Procedure Device Hubs; X. Uses, and XI. Device Placement Systems.

I. Power Supply

The energy utilized within the energy delivery systems is supplied through a power supply. The technology is not limited to a particular type or kind of power supply. In some embodiments, the power supply is configured to provide energy to one or more components of the energy delivery systems (e.g., energy delivery device). The power supply is not limited to providing a particular type of energy (e.g., radiofrequency energy, microwave energy, radiation energy, laser, focused ultrasound, etc.). However, in some preferred embodiments, microwave energy is employed. The power supply is not limited to providing particular amounts of energy or at a particular rate of delivery. In some embodiments, the power supply is configured to provide energy to an energy delivery device for purposes of tissue ablation.

In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the type of energy provided with the power supply is microwave energy. In some embodiments, the power supply provides microwave energy to ablation devices for purposes of tissue ablation. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction as it radiates through tissue, fluid/blood, as well as air. Therefore, microwave energy can be used in tissue, lumens, lungs, and intravascularly.

In some embodiments, the power supply is an energy generator. In some embodiments, the generator is configured to provide as much as 100 watts of microwave power of a frequency of from 915 MHz to 5.8 GHz, although the present invention is not so limited. In some embodiments, a conventional magnetron of the type commonly used in microwave ovens is chosen as the generator. In some embodiments, a single-magnetron based generator (e.g., with an ability to output 300 W through a single channel, or split into multiple channels) is utilized. It should be appreciated, however, that any other suitable microwave power source can substituted in its place. In some embodiments, the types of generators include, but are not limited to, those available from Cober-Muegge, LLC, Norwalk, Conn., USA, Sairem generators, and Gerling Applied Engineering generators. In some embodiments, the generator has at least approximately 60 Watts available (e.g., 50, 55, 56, 57, 58, 59, 60, 61, 62, 65, 70, 100, 500, 1000 Watts). For a higher-power operation, the generator is able to provide approximately 300 Watts (e.g., 200 Watts, 280, 290, 300, 310, 320, 350, 400, 750 Watts). In some embodiments, wherein multiple antennas are used, the generator is able to provide as much energy as necessary (e.g., 400 Watts, 500, 750, 1000, 2000, 10,000 Watts). In some embodiments, the generator comprises solid state amplifier modules which can be operated separately and phase-controlled. In some embodiments, generator outputs are combined constructively to increase total output power. In some embodiments, the power supply distributes energy (e.g., collected from a generator) with a power distribution system. The present invention is not limited to a particular power distribution system. In some embodiments, the power distribution system is configured to provide energy to an energy delivery device (e.g., a tissue ablation catheter) for purposes of tissue ablation. The power distribution system is not limited to a particular manner of collecting energy from, for example, a generator. The power distribution system is not limited to a particular manner of providing energy to ablation devices. In some embodiments, the power distribution system is configured to transform the characteristic impedance of the generator such that it matches the characteristic impedance of an energy delivery device (e.g., a tissue ablation catheter).

In some embodiments, the power distribution system is configured with a variable power splitter so as to provide varying energy levels to different regions of an energy delivery device or to different energy delivery devices (e.g., a tissue ablation catheter). In some embodiments, the power splitter is provided as a separate component of the system. In some embodiments, the power splitter is used to feed multiple energy delivery devices with separate energy signals. In some embodiments, the power splitter electrically isolates the energy delivered to each energy delivery device so that, for example, if one of the devices experiences an increased load as a result of increased temperature deflection, the energy delivered to that unit is altered (e.g., reduced, stopped) while the energy delivered to alternate devices is unchanged. The present invention is not limited to a particular type or kind of power splitter. In some embodiments, the power splitter is designed by SM Electronics. In some embodiments, the power splitter is configured to receive energy from a power generator and provide energy to additional system components (e.g., energy delivery devices). In some embodiments the power splitter is able to connect with one or more additional system components. In some embodiments, the power splitter is configured to deliver variable amounts of energy to different regions within an energy delivery device for purposes of delivering variable amounts of energy from different regions of the device. In some embodiments, the power splitter is used to provide variable amounts of energy to multiple energy delivery devices for purposes of treating a tissue region. In some embodiments, the power splitter is configured to operate within a system comprising a processor, an energy delivery device, a temperature adjustment system, a power splitter, a tuning system, and/or an imaging system. In some embodiments, the power splitter is able to handle maximum generator outputs plus, for example, 25% (e.g., 20%, 30%, 50%). In some embodiments, the power splitter is a 1000-watt-rated 2-4 channel power splitter.

In some embodiments, where multiple antennas are employed, the system may be configured to run them simultaneously or sequentially (e.g., with switching). In some embodiments, the system is configured to phase the fields for constructive or destructive interference. Phasing may also be applied to different elements within a single antenna. In some embodiments, switching is combined with phasing such that multiple antennas are simultaneously active, phase controlled, and then switched to a new set of antennas (e.g., switching does not need to be fully sequential). In some embodiments, phase control is achieved precisely. In some embodiments, phase is adjusted continuously so as to move the areas of constructive or destructive interference in space and time. In some embodiments, the phase is adjusted randomly. In some embodiments, random phase adjustment is performed by mechanical and/or magnetic interference.

II. Energy Delivery Devices

The energy delivery systems contemplate the use of any type of energy delivery device configured to deliver (e.g., emit) energy (e.g., ablation device, surgical device, etc.) (see, e.g., U.S. Pat. Nos. 9,119,649, 9,072,532, 8,672,932, 7,467,015, 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International patent Application Nos. WO2011/140087, WO 06/008481, WO 06/002943, WO 05/034783, WO 04/112628, WO 04/033039, WO 04/026122, WO 03/088858, WO 03/039385 WO 95/04385; each herein incorporated by reference in their entireties).

In some embodiments, antennae configured to emit energy comprise coaxial transmission lines. The devices are not limited to particular configurations of coaxial transmission lines. Examples of coaxial transmission lines include, but are not limited to, coaxial transmission lines developed by Pasternack, Micro-coax, and SRC Cables. In some embodiments, the coaxial transmission line has an inner (i.e., center) conductor, a dielectric element, and an outer conductor (e.g., outer shield). In some embodiments, the systems utilize antennae having flexible coaxial transmission lines (e.g., for purposes of positioning around, for example, pulmonary veins or through tubular structures) (see, e.g., U.S. Pat. Nos. 7,033,352, 6,893,436, 6,817,999, 6,251,128, 5,810,803, 5,800,494; each herein incorporated by reference in their entireties).

In some embodiments, the energy delivery devices have a triaxial transmission line. In some embodiments, a triaxial microwave probe design has an outermost conductor that allows improved tuning of the antenna to reduce reflected energy through the transmission line. This improved tuning reduces heating of the transmission line allowing more power to be applied to the tissue and/or a smaller transmission line (e.g. narrower) to be used. Further, the outer conductor may slide with respect to the inner conductors to permit adjustment of the tuning to correct for effects of the tissue on the tuning. In some embodiments, a device comprising first, second, and third conductors is sufficiently flexible to navigate a winding path (e.g. through a branched structure within a subject (e.g. through the brachial tree)). In some embodiments, the first and second conductors may fit slidably within the third conductor.

In some embodiments, one or more components of a coaxial transmission line or triaxial transmission line comprise a flexible and/or collapsible material (e.g. biaxially-oriented polyethylene terephthalate (boPET) (e.g. MYLAR, MELINEX, HOSTAPHAN, etc.), etc.). In some embodiments, the outer conductor of the coaxial transmission line (or second (middle) conductor of a triaxial transmission line) comprises a flexible and/or collapsible material (e.g. boPET). In some embodiments, a component of a coaxial transmission line (e.g. outer conductor) comprises boPET coated in one or more films to provide desired characteristics (e.g. electric conductivity, heat insulation, etc.). In some embodiments, a collapsible outer conductor allows the transmission line to adopt variable cross-sectional profile (e.g. variable diameter, variable shape, etc.). In some embodiments, a collapsible outer conductor encircles the inner conductor. In some embodiments, a collapsible outer conductor forms a closed sack around the inner conductor. In some embodiments, fluid (e.g. dielectric material, and/or coolant) can be flowed through the collapsible outer conductor to adjust its variable cross-sectional profile. In some embodiments, a collapsible outer conductor adopts a collapsed conformation when fluid is withdrawn from the area within the outer conductor, thereby decreasing the pressure within the outer conductor. In some embodiments, in a collapsed conformation the outer conductor displays a minimized cross-sectional profile. In some embodiments, in a collapsed conformation the outer conductor closely hugs the periphery of the inner conductor. In some embodiments, the collapsed conformation provides decreased cross-sectional profile and/or increased flexibility to aid in insertion, placement, and/or withdrawal of the coaxial transmission line. In some embodiments, a collapsible outer conductor adopts an expanded conformation when fluid is flowed into the area within the outer conductor, thereby increasing the pressure within the outer conductor. In some embodiments, in an expanded conformation the outer conductor displays a maximized cross-sectional profile. In some embodiments, in an expanded conformation the distance between the inner conductor and the outer conductor is maximized. In some embodiments, the expanded conformation provides increased cross-sectional profile and/or optimized conduction to aid in energy delivery along the coaxial transmission line. In some embodiments, the expanded conformation provides an increased volume of coolant along the coaxial transmission line. In some embodiments, the collapsible outer conductor adopts any suitable shape in the expanded conformation. In some embodiments, the coaxial transmission line runs through a lumen, the shape of which dictates the expanded shape of the collapsible outer conductor. In some embodiments, the collapsible outer conductor adopts any suitable shape in the collapsed conformation. In some embodiments, the shape or configuration of the dielectric material dictates the collapsed shape of the collapsible outer conductor. In some embodiments, a collapsible outer conductor also comprises a coolant sheath, as described herein.

In some embodiments, the dielectric material core is shaped to provide to provide channels within the dielectric space (e.g. air channels, coolant channels, vacant channels, etc.). In some embodiments, channels are completely or partially encompassed by the dielectric material. In some embodiments, the dielectric material divides the dielectric space into channels to create a "wagon wheel" conformation. In some embodiments, the dielectric material divides the dielectric space (e.g. the space between the inner and outer conductors) into 1 or more channels (e.g. 1, 2, 3, 4, 5, 6, 7, 8, 9, 10, or more channels). In some embodiments, the channels within the dielectric space serve as coolant channels. In some embodiments, the channels within the dielectric space house coolant tubes. In some embodiments, a coolant tube within a channel delivers coolant along the transmission line, and a coolant channel provides the return path, to the proximal end of the transmission line. In some embodiments, a channel comprises multiple coolant tubes (e.g. coolant and return). In some embodiment, channels formed by the dielectric material comprise a non-metallic filler. In some embodiments, non-metallic filler resides in the channels in the distal region of the transmission line (e.g. beyond the end of the outer conductor).

In some embodiments, the energy delivery devices are provided with a proximal portion and a distal portion, wherein the distal portion is detachable and provided in a variety of different configurations that can attach to a proximal portion. For example, in some embodiments, the proximal portion comprises a handle and an interface to other components of the system (e.g., power supply) and the distal portion comprises a detachable antenna having desired properties. A plurality of different antenna configured for different uses may be provided and attached to the handle unit for the appropriate indication.

In some embodiments, the energy delivery devices have therein protection sensors designed to prevent undesired use of the energy delivery devices. The energy delivery devices are not limited to a particular type or kind of protection sensors. In some embodiments, the energy delivery devices have therein a temperature sensor designed to measure the temperature of, for example, the energy delivery device and/or the tissue contacting the energy delivery device. In some embodiments, as a temperature reaches a certain level the sensor communicates a warning to a user via, for example, the processor. In some embodiments, the energy delivery devices have therein a skin contact sensor designed to detect contact of the energy delivery device with skin (e.g., an exterior surface of the skin). In some embodiments, upon contact with undesired skin, the skin contact sensor communicates a warning to a user via, for example, the processor. In some embodiments, the energy delivery devices have therein an air contact sensor designed to detect contact of the energy delivery device with ambient air (e.g., detection through measurement of reflective power of electricity passing through the device). In some embodiments, upon contact with undesired air, the skin contact sensor communicates a warning to a user via, for example, the processor. In some embodiments, the sensors are designed to prevent use of the energy delivery device (e.g., by automatically reducing or preventing power delivery) upon detection of an undesired occurrence (e.g., contact with skin, contact with air, undesired temperature increase/decrease). In some embodiments, the sensors communicate with the processor such that the processor displays a notification (e.g., a green light) in the absence of an undesired occurrence. In some embodiments, the sensors communicate with the processor such that the processor displays a notification (e.g., a red light) in the presence of an undesired occurrence and identifies the undesired occurrence.

In some embodiments, the energy delivery devices are used above a manufacturer's recommended power rating. In some embodiments, cooling techniques described herein are applied to permit higher power delivery. The present invention is not limited to a particular amount of power increase. In some embodiments, power ratings exceed manufacturer's recommendation by 5× or more (e.g., 5×, 6×, 10×, 15×, 20×, etc.).

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249; each herein incorporated by reference in their entireties. In some embodiments, the anchoring element has a circulating agent (e.g. a gas delivered at or near its critical point; $CO_2$) that freezes the interface between antenna and tissue thereby sticking the antenna in place. In such embodiments, as the tissue melts the antenna remains secured to the tissue region due to tissue desiccation.

In some embodiments, the devices are used in the ablation of a tissue region having high amounts of air and/or blood flow (e.g., pulmonary tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

Thus, in some embodiments, the systems, devices, and methods of the present invention provide an ablation device coupled with a component that provides occlusion of a passageway (e.g., bronchial occlusion). The occlusion component (e.g., inflatable balloon) may be directly mounted on the ablation system or may be used in combination with another component (e.g., an endotracheal or endobronchial tube) associated with the system.

In some embodiments, the devices may be mounted onto additional medical procedure devices. For example, the devices may be mounted onto endoscopes, intravascular catheters, bronchoscopes, or laproscopes. In some embodiments, the devices are mounted onto steerable catheters. In some embodiments, a flexible catheter is mounted on an endoscope, intravascular catheter or laparoscope. For example, the flexible catheter, in some embodiments, has multiple joints (e.g., like a centipede) that permits bending and steering as desired to navigate to the desired location for treatment. In some embodiments, devices are deployed through endoscopes, intravascular catheters, bronchoscopes, or laproscopes.

In some embodiments, the energy delivery systems of the present invention utilize devices configured for delivery of microwave energy with an optimized characteristic impedance. Such devices are configured to operate with a characteristic impedance of 50Ω or higher (e.g., between 50 and 90Ω; e.g., 50, 55, 56, 57, 58, 59, 60, 61, 62, . . . 90Ω, preferably at 77Ω). However, in other embodiments (e.g., where a larger inner conductor is employed), characteristic impedance of less than 50Ω is employed. In some embodiments, optimized characteristic impedance is achieved through selection of (or absence of) an appropriate dielectric material.

In some embodiments, the energy delivery device comprises an antenna comprising an inner conductor; and a conductive tip at a distal end of said antenna; wherein the inner conductor is not physically coupled to said conductive tip (e.g., wherein the inner conductor is capactively-coupled to the conductive tip) (see e.g., U.S. Pat. Publ. No. 2013/0165915, herein incorporated by reference in its entirety). In some embodiments, the antenna comprises a conductive outer conductor surrounding at least a portion of the inner conductor. In some embodiments, the conductive tip comprises a trocar.

A cross-sectional view of an embodiment of an energy delivery device optimized and tested for endobronchial or transbronchial delivery for ablative energy to lung tissues is shown in FIG. 1. The outermost layer is jacket. The jacket is preferably heat sealed to minimize heat transfer from inside the energy delivery device to outside the device and any tissues contacted or in the vicinity thereof. The jacket may be made of any desired material. In some embodiments, the jacket comprises polyester.

The next layer inward is a shield (e.g., external conductor). The shield assists in minimizing heat transfer from inside the energy delivery device to outside the device and any tissues contacted or in the vicinity thereof. The shield also provide an outer conductor or an intermediate conductor in a coaxial or triaxial transmission line. The shield may be made of any desired material. In some embodiments, the shield comprises one or more electrically conductive materials, such as metals. In some embodiments, the shield is copper. In some embodiments, the shield is plated copper. In some embodiments, the plating is silver. In some embodiments, the outer conductor is constructed of braided or jointed material to provide both strength and flexibility.

The next layer inward is a non-conducting core tube. The core tube may be entirely a dielectric material. One or more channels may be present in the material. In some embodiments, the core tube comprises a plastic. In some embodiments, the core tube comprises a fluoropolymer. In some embodiments, the fluoropolymer is a semi-crystalline fully-fluorinated melt processable fluoropolymer (e.g., MFA (Solvay)).

The next layer inward is an air gap containing a monofilament tubing separating and spacing the core from an inner conductor. In some embodiments, a plurality of tubes are provided (e.g., two, three, four, etc.). In some embodiments, the tube or tubes are helically wrapped around the inner conductor. The tubes may be made of any desired material, preferably non-conductive. In some embodiments, the tubes are plastic. In some embodiments, the tubes are perfluoroalkoxy alkane (PFA) tubes.

The next layer inward is an inner conductor. The inner conductor may be made of any desired conductive material. In some embodiments, the inner conductor is copper. In some embodiments, the inner conductor is annealed copper. In some embodiments, the inner conductor is hollow, containing a passageway in its center that permits transfer of fluids (e.g., gaseous or liquid coolants) along the length of the inner conductor.

The absolute and relative dimensions of each layer may be selected as desired. Preferably the outer diameter is sufficiently small to allow entry of the antenna into the small airways of the internal lung or other desired biological areas to be targeted. Exemplary dimensions are shown in FIG. 1 with the outer diameter measured at the outside of the jacket layer being 1.65 mm (+/−0.05 mm), the diameter at the outer edge of the shield of 1.6 mm (+/−0.05 mm), the diameter at the outer edge of the core of 1.4 mm (+/−0.025 mm), and the diameter at the inner edge of the core of 1.0 mm (+/−0.025 mm). In some embodiments, the antenna or its individual layers are larger or smaller than those exemplified in FIG. 1 (e.g., 5%, 10%, 20%, 30%, 40%, 50%, 60%, 70%, 80%, 90%, etc.).

Figure 2:
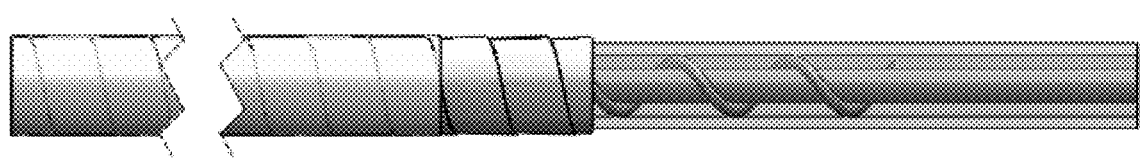
FIG. 2 shows a cutaway view of an energy delivery device with coolant channels.

FIG. 2 shows an exemplary energy delivery of FIG. 1 shown length-wise with a cutaway view showing the internal components.

Figure 3A:
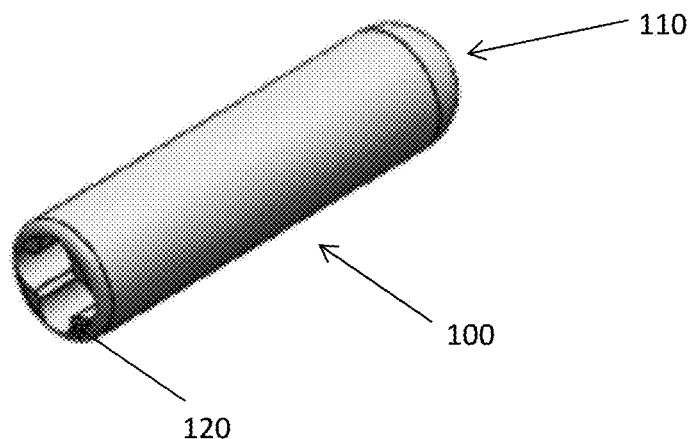
FIGS. 3A-C show a coolant flow reversal cap.

In some embodiments, the internal conductor terminates at its distal end with a coolant flow exchanger in the form of a gas return pin. The pin has a proximal end with an opening and a closed distal end. The opening at the proximal end is sized to receive the inner conductor. The opening is further sized to provide one or more channels that are exterior to an inner conductor inserted into the opening. The outer diameter of the pin is sized to fit within the core. The hollow inner conductor terminates within the pin such that coolant flowing out of the distal end of the internal conductor enters the opening within the pin, and is returned through the one or more channels towards the proximal end of the pin. Coolant emerging out of the channels moves into the air space between the inner conductor and the core. The presence of the monofilament tubing in the this region creates one or more channels (e.g., a spiral channel) along the length of the energy delivery device, provide a large surface area for the coolant as it moves distal to proximal along the energy delivery device. In some embodiments, the coolant path is reversed, initially traveling proximal to distal along the air gap between the inner conductor and core and reversed in the cap into the hollow pathway of the inner conductor where it returns distal to proximal along the energy delivery device. The cap may be made of any desired material and may be conductive or non-conductive. In some embodiments, the cap is made of brass. An exemplary cap 100 is shown in FIGS. 3A-D. FIG. 3A shows an exterior view of a cap with a rounded distal tip 110. The interior of the cap comprises four ridges 120 that span the length of the interior of the cap. The ridges create four coolant return channels

Figure 3B:
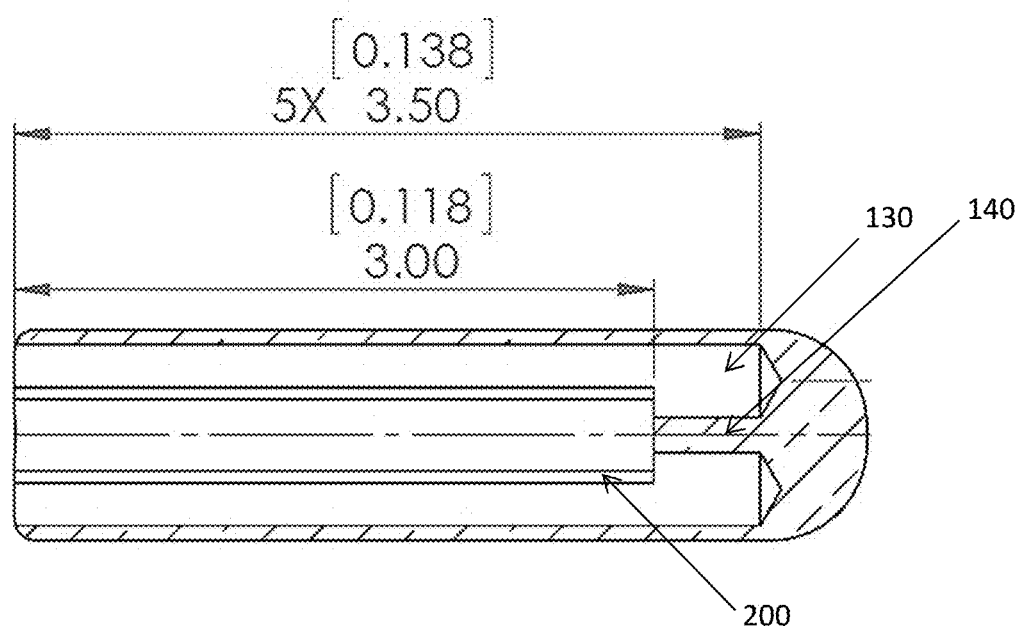
Figure 3C:
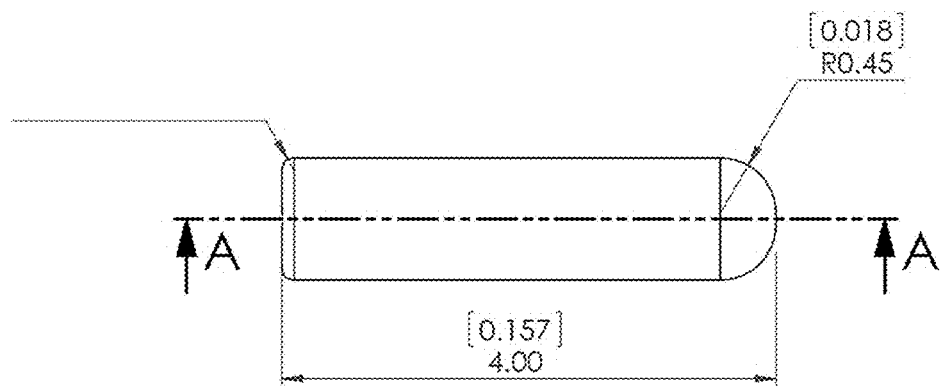

130 when an inner conductor is inserted into the cap. FIG. 3B shows an interior cut-away structure of the cap having a hollow inner conductor 200 inserted therein. The interior of the cap comprises a stop 140 to position the distal end of the inner conductor. In some embodiments, the stop is non-conductive to prevent electrical flow from the inner conductor to the cap. In some embodiments, the stop is conductive, allowing electrical flow from the inner conductor to the cap. Exemplary dimensions in mm and inches (in brackets) are provided. FIG. 3C shows exemplary dimensions of the exterior of the cap.

Figure 4A:
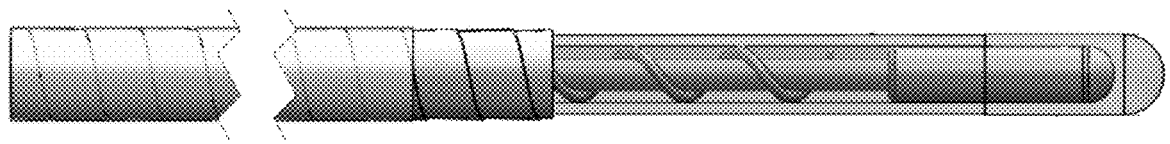
FIGS. 4A-B show an energy delivery device with coolant flow reversal cap.
Figure 4B:
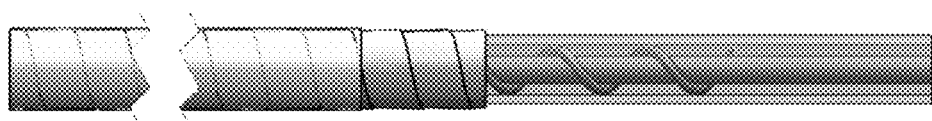
Figure 4B:
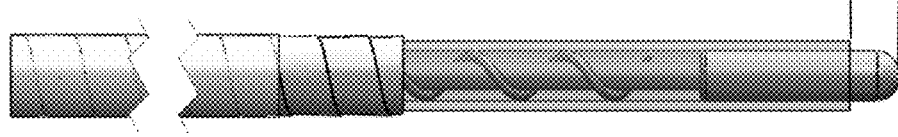
Figure 4B:
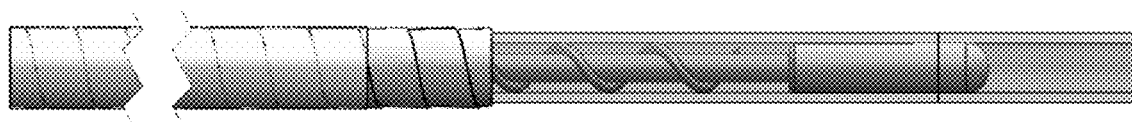

FIG. 4A shows a cutaway view of an energy delivery device with a cap inserted therein. FIG. 4B shows an exemplary manufacturing process for inserting the cap. The top panel shows an energy delivery device terminating at the inner conductor. The middle panel shows insertion of the cap over the inner conductor with its distal end extending beyond the end of the energy delivery device (1 mm in this example). The lower panel shows addition of material to form the exterior tip of energy delivery device. The formed round tip of the energy delivery device is shown in FIG. 4A. In some embodiments, a trocar or other tissue-penetrating tip is attached over the round tip (not shown).

Figure 5:
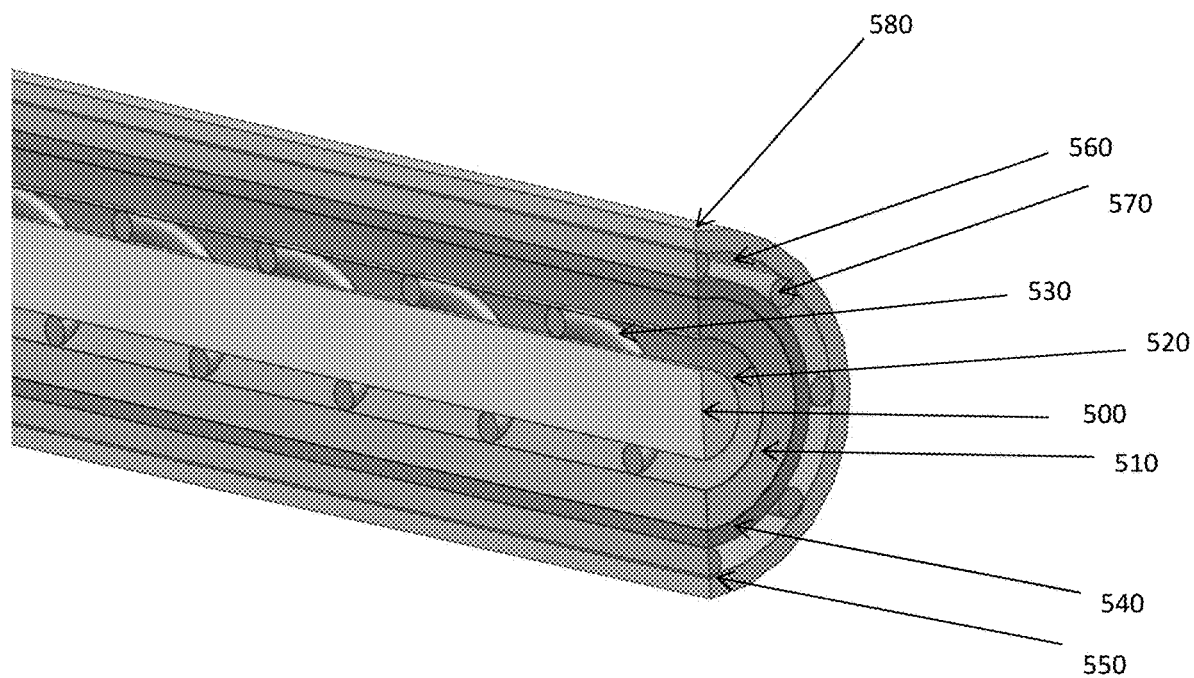
FIG. 5 shows a cross-sectional view of an energy delivery device with coolant channels, some of which are exterior to the outer conductor.

A variety of alternative coolant management systems may be used. FIG. 5 shows one example providing a cross-sectional view of an energy delivery device. In this embodiment, the inner conductor 500 is solid rather than hollow. A core 510 creates an air space 520 between the core and the inner conductor 500. A monofilament tube 530 spiraled around the inner conductor within the air space adapts the air space 520 as a spiral channel. An outer conductor 540 is exterior to the core 520. In this design, an outer jacket 550 is provided around the outer conductor. The outer jacket may be made of non-conductive insulating material or may be conductive (forming a triaxial antenna with the outer conductor and inner conductor). An air gap 560 is created between the outer jacket and the outer conductor. The air gap 560 is transformed into a plurality of channels by the addition of spacer tubing 570. In some such embodiments, coolant is flowed proximal to distal along the air gap 520. Coolant is returned distal to proximal via the air gap 560.

Figure 6:
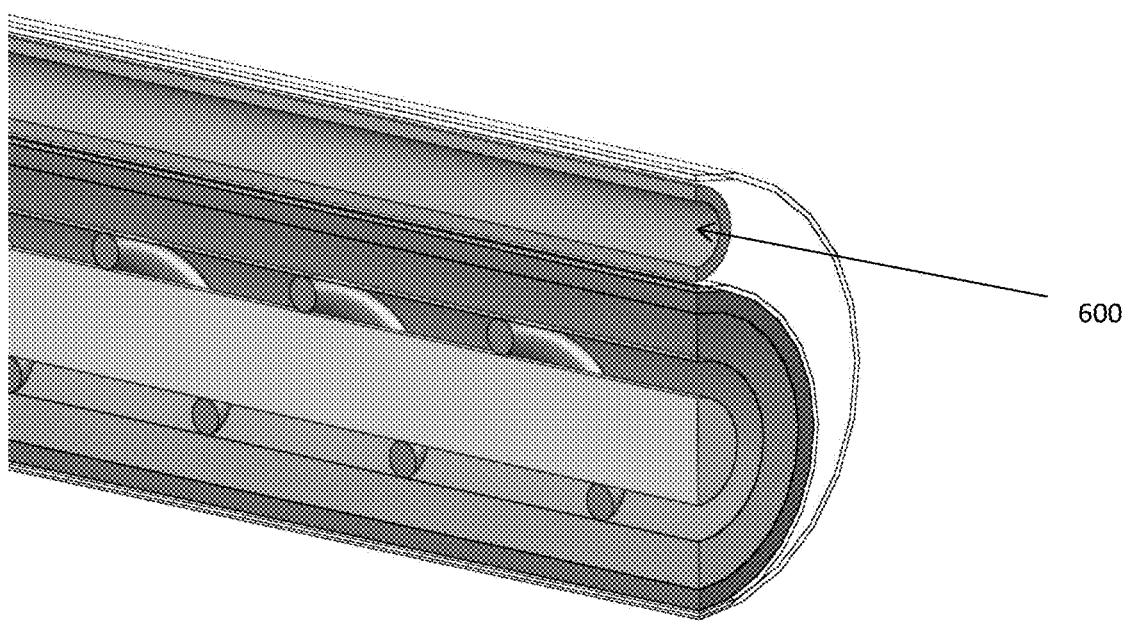
FIG. 6 shows a cross-sectional view of an energy delivery device with a coolant tube exterior to the outer conductor.

Another embodiment is shown in FIG. 6. In this embodiment, a gas inlet tube 600 is provided between the outer conductor and the outer jacket. Coolant is flowed proximal to distal through the gas inlet tube 600 and returned in the air space between the inner conductor and the core.

III. Processor

In some embodiments, the energy delivery systems utilize processors that monitor and/or control and/or provide feedback concerning one or more of the components of the system. In some embodiments, the processor is provided within a computer module. The computer module may also comprise software that is used by the processor to carry out one or more of its functions. For example, in some embodiments, the systems provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428; each of which is herein incorporated by reference in their entireties). In some embodiments, the software is configured to provide information (e.g., monitoring information) in real time. In some embodiments, the software is configured to interact with the energy delivery systems such that it is able to raise or lower (e.g., tune) the amount of energy delivered to a tissue region. In some embodiments, the software is designed to prime coolants for distribution into, for example, an energy delivery device such that the coolant is at a desired temperature prior to use of the energy delivery device. In some embodiments, the type of tissue being treated (e.g., lung) is inputted into the software for purposes of allowing the processor to regulate (e.g., tune) the delivery of microwave energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics. In some embodiments, the processor is operated by remote control.

In some embodiments, the processor is used to generate, for example, an ablation chart based upon entry of tissue characteristics (e.g., tumor type, tumor size, tumor location, surrounding vascular information, blood flow information, etc.). In such embodiments, the processor directs placement of the energy delivery device so as to achieve desired ablation based upon the ablation chart. In some embodiments, a processor communicates with positions sensors and/or steering mechanisms to provide appropriate placement of systems and devices.

In some embodiments a software package (e.g., embodied in any desired form of non-transitory computer readable media) is provided to interact with the processor that allows the user to input parameters of the tissue to be treated (e.g., type of tumor or tissue section to be ablated, size, where it is located, location of vessels or vulnerable structures, and blood flow information) and then draw the desired ablation zone on a CT or other image to provide the desired results. The probes may be placed into the tissue, and the computer generates the expected ablation zone based on the information provided. Such an application may incorporate feedback. For example, CT, MRI, or ultrasound imaging or thermometry may be used during the ablation. This data is fed back into the computer, and the parameters readjusted to produce the desired result.

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP® disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks.

As used herein, the terms "processor" and "central processing unit" or "CPU" are used interchangeably and refer to a device that is able to read a program from a computer memory device (e.g., ROM or other computer memory) and perform a set of steps according to the program.

IV. Imaging Systems

In some embodiments, the energy delivery systems utilize imaging systems comprising imaging devices and/or software. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems provide software is configured for use of imaging equipment (e.g., CT, MRI, ultrasound). In some embodiments, the imaging equipment software allows a user to make predictions based upon known thermodynamic and electrical properties of tissue, vasculature, and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the imaging systems are used to monitor ablation procedures (e.g., microwave thermal ablation procedures, radio-frequency thermal ablation procedures). The present invention is not limited to a particular type of monitoring. In some embodiments, the imaging systems are used to monitor the amount of ablation occurring within a particular tissue region(s) undergoing a thermal ablation procedure. In some embodiments, the monitoring operates along with the ablation devices (e.g., energy delivery devices) such that the amount of energy delivered to a particular tissue region is dependent upon the imaging of the tissue region. The imaging systems are not limited to a particular type of monitoring. The present invention is not limited to what is being monitored with the imaging devices. In some embodiments, the monitoring is imaging blood perfusion for a particular region so as to detect changes in the region, for example, before, during and after a thermal ablation procedure. In some embodiments, the monitoring includes, but is not limited to, MRI imaging, CT imaging, ultrasound imaging, nuclear medicine imaging, and fluoroscopy imaging. For example, in some embodiments, prior to a thermal ablation procedure, a contrast agent (e.g., iodine or other suitable CT contrast agent; gadolinium chelate or other suitable MRI contrast agent, microbubbles or other suitable ultrasound contrast agent, etc.) is supplied to a subject (e.g., a patient) and the contrast agent perfusing through a particular tissue region that is undergoing the ablation procedure is monitored for blood perfusion changes. In some embodiments, the monitoring is qualitative information about the ablation zone properties (e.g., the diameter, the length, the cross-sectional area, the volume). The imaging system is not limited to a particular technique for monitoring qualitative information. In some embodiments, techniques used to monitor qualitative information include, but are not limited to, non-imaging techniques (e.g., time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices). In some embodiments, the interstitial device provides a signal and/or detection for imaging (e.g., electro-acoustic imaging, electromagnetic imaging, electrical impedance tomography). In some embodiments, non-imaging techniques are used to monitor the dielectric properties of the medium surrounding the antenna, detect an interface between the ablated region and normal tissue through several means, including resonance frequency detection, reflectometry or distance-finding techniques, power reflection/transmission from interstitial antennas or external antennas, etc. In some embodiments, the qualitative information is an estimate of ablation status, power delivery status, and/or simple go/no-go checks to ensure power is being applied. In some embodiments, the imaging systems are designed to automatically monitor a particular tissue region at any desired frequency (e.g., per second intervals, per one-minute intervals, per ten-minute intervals, per hour-intervals, etc.). In some embodiments, the present invention provides software designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the energy delivery devices. Likewise, an algorithm may be applied to predict the shape and size of the tissue region to be ablated (e.g., tumor shape) such that the system recommends the type, number, and location of ablation probes to effectively treat the region. In some embodiments, the system is configured to with a navigation or guidance system (e.g., employing triangulation or other positioning routines) to assist in or direct the placement of the probes and their use.

For example, such procedures may use the enhancement or lack of enhancement of a contrast material bolus to track the progress of an ablation or other treatment procedure. Subtraction methods may also be used (e.g., similar to those used for digital subtraction angiography). For example, a first image may be taken at a first time point. Subsequent images subtract out some or all of the information from the first image so that changes in tissue are more readily observed. Likewise, accelerated imaging techniques may be used that apply "under sampling" techniques (in contrast to Nyquist sampling). It is contemplated that such techniques provide excellent signal-to-noise using multiple low resolutions images obtained over time. For example, an algorithm called HYPER (highly constrained projection reconstruction) is available for MM that may be applied to embodiments of the systems of the invention.

As thermal-based treatments coagulate blood vessels when tissue temperatures exceed, for example, 50° C., the coagulation decreases blood supply to the area that has been completely coagulated. Tissue regions that are coagulated do not enhance after the administration of contrast. In some embodiments, the present invention utilizes the imaging systems to automatically track the progress of an ablation procedure by giving, for example, a small test injection of contrast to determine the contrast arrival time at the tissue region in question and to establish baseline enhancement. In some embodiments, a series of small contrast injections is next performed following commencement of the ablation procedure (e.g., in the case of CT, a series of up to fifteen 10 ml boluses of 300 mgI/ml water soluble contrast is injected), scans are performed at a desired appropriate post-injection time (e.g., as determined from the test injection), and the contrast enhancement of the targeted area is determined using, for example, a region-of-interest (ROI) to track any one of a number of parameters including, but not limited to, attenuation (Hounsfield Units [HU]) for CT, signal (MRI), echogenicity (ultrasound), etc. The imaged data is not limited to a particular manner of presentation. In some embodiments, the imaging data is presented as color-coded or grey scale maps or overlays of the change in attenuation/signal/echogenicity, the difference between targeted and non-targeted tissue, differences in arrival time of the contrast bolus during treatment, changes in tissue perfusion, and any other tissue properties that can be measured before and after the injection of contrast material. The methods of the present invention are not limited to selected ROI's, but can be generalized to all pixels within any image. The pixels can be color-coded, or an overlay used to demonstrate where tissue changes have occurred and are occurring. The pixels can change colors (or other properties) as the tissue property changes, thus giving a near real-time display of the progress of the treatment. This method can also be generalized to 3d/4d methods of image display.

In some embodiments, the area to be treated is presented on a computer overlay, and a second overlay in a different color or shading yields a near real-time display of the progress of the treatment. In some embodiments, the presentation and imaging is automated so that there is a feedback loop to a treatment technology (RF, MW, HIFU, laser, cryo, etc) to modulate the power (or any other control parameter) based on the imaging findings. For example, if the perfusion to a targeted area is decreased to a target level, the power could be decreased or stopped. For example, such embodiments are applicable to a multiple applicator system as the power/time/frequency/duty cycle, etc. is modulated for each individual applicator or element in a phased array system to create a precisely sculpted zone of tissue treatment. Conversely, in some embodiments, the methods are used to select an area that is not to be treated (e.g., vulnerable structures that need to be avoided such as bile ducts, bowel, etc.). In such embodiments, the methods monitor tissue changes in the area to be avoided, and warn the user (e.g., treating physician) using alarms (e.g., visible and/or audible alarms) that the structure to be preserved is in danger of damage. In some embodiments, the feedback loop is used to modify power or any other parameter to avoid continued damage to a tissue region selected not to be treated. In some embodiments, protection of a tissue region from ablation is accomplished by setting a threshold value such as a target ROI in a vulnerable area, or using a computer overlay to define a "no treatment" zone as desired by the user.

V. Tuning Systems

In some embodiments, the energy delivery systems utilize tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957,969, 5,405,346; each herein incorporated by reference in their entireties). In some embodiments, the device is pretuned to the desired tissue and is fixed throughout the procedure. In some embodiments, the tuning system is designed to match impedance between a generator and an energy delivery device (see, e.g., U.S. Pat. No. 5,364,392; herein incorporated by reference in its entirety). In some embodiments, the tuning element is automatically adjusted and controlled by a processor. In some embodiments, a processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas or blood vessels, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

VI. Temperature Adjustment Systems

In some embodiments, the energy delivery systems utilize coolant systems so as to reduce undesired heating within and along an energy delivery device (e.g., tissue ablation catheter). The systems are not limited to a particular cooling system mechanism. In some embodiments, the systems are designed to circulate a coolant (e.g., air, liquid, etc.) throughout an energy delivery device such that the coaxial transmission line(s) or triaxial transmission line(s) and antenna(e) temperatures are reduced.

In some embodiments, energy delivery devices utilize reduced temperature energy patterns to reduce undesired heating along the length of the transmission line. In some embodiments, constant low power energy transmission provides sufficient energy at the target site (e.g. sufficient for effective tumor ablation) without undue heating along the path of the transmission line. In some embodiments, energy is delivered in a pulse pattern to provide bursts of sufficient energy at the target site (e.g. sufficient for effective tumor ablation) with less heat build-up along the transmission line than continuous delivery. In some embodiments, the length and intensity of the pulse-pattern are set by monitoring temperature along the transmission line or in the tissue surrounding the transmission line. In some embodiments, a pulse pattern is predetermined to balance the amount of energy delivered to the target site with the amount of heat release along the transmission line. In some embodiments, any suitable pulse pattern will find use with the devices, systems, and methods of the present invention. In some embodiments, an ablation algorithm is calculated or determined based on a combination of time (e.g. of treatment, of pulses, of time between pulses), power (e.g. power generated, power delivered, power lost, etc.), and temperature monitoring.

In some embodiments, the flow of coolant is monitored to assess and control temperature. For example, the pressure of coolant exhaust through a fixed sized chamber may be monitored. By measuring the in-flow and out-flow differential, coolant performance can be assessed. Should any parameter fall out of an acceptable performance range, an alarm may be sounded and the system controls altered as desired (emergency off, etc.).

In some embodiments, an energy delivery device comprises a capacitor and/or energy gate at the distal end of the transmission line. The capacitor and/or gate delivers energy (e.g. microwave energy) to the target site once a threshold of energy has built up behind the capacitor and/or gate. Low level energy is delivered along the transmission line, thereby reducing heat build-up along the pathway. Once sufficient energy has built up at the capacitor and/or gate, a high energy burst of energy (e.g. microwave energy) is delivered to the target site. The capacitor and/or gate delivery method has the advantage of reduced heating along the transmission path due to the low level energy transfer, as well as bursts of high energy being delivered at the target site (e.g. sufficient for tumor ablation).

In some embodiments, all or a portion of the energy generating circuitry is located at one or more points along the transmission line. In some embodiments, all or a portion of the microwave generating circuitry is located at one or more points along the transmission line. In some embodiments, generating energy (e.g. microwave energy) at one or more points along the transmission line reduces the distance the energy needs to travel, thereby reducing energy loss, and undesired heat generation. In some embodiments, generating energy (e.g. microwave energy) at one or more points along the transmission line allows for operating at reduced energy levels while providing the same energy level to the treatment site.

VII. Identification Systems

In some embodiments, the energy delivery systems utilize identification elements (e.g., RFID elements, identification rings (e.g., fidicials), barcodes, etc.) associated with one or more components of the system. In some embodiments, the identification element conveys information about a particular component of the system. The present invention is not limited by the information conveyed. In some embodiments, the information conveyed includes, but is not limited to, the type of component (e.g., manufacturer, size, energy rating, tissue configuration, etc.), whether the component has been used before (e.g., so as to ensure that non-sterile components are not used), the location of the component, patient-specific information and the like. In some embodiments, the information is read by a processor of the present invention. In some such embodiments, the processor configures other components of the system for use with, or for optimal use with, the component containing the identification element.

In some embodiments, the energy delivery devices have thereon markings (e.g., scratches, color schemes, etchings, painted contrast agent markings, radiopaque bands, identification rings (e.g., fidicials), and/or ridges) so as to improve identification of a particular energy delivery device (e.g., improve identification of a particular device located in the vicinity of other devices with similar appearances). The markings find particular use where multiple devices are inserted into a patient. In such cases, particularly where the devices may cross each other at various angles, it is difficult for the treating physician to associate which proximal end of the device, located outside of the patient body, corresponds to which distal end of the device, located inside the patient body. In some embodiments, a marking (e.g., a number) a present on the proximal end of the device so that it is viewable by the physician's eyes and a second marking (e.g., that corresponds to the number) is present on the distal end of the device so that it is viewable by an imaging device when present in the body. In some embodiments, where a set of antennas is employed, the individual members of the set are numbered (e.g., 1, 2, 3, 4, etc.) on both the proximal and distal ends. In some embodiments, handles are numbered, a matching numbered detachable (e.g., disposable) antennas are connected to the handles prior to use. In some embodiments, a processor of the system ensures that the handles and antennas are properly matched (e.g., by RFID tag or other means). In some embodiments, where the antenna are disposable, the system provides a warning if a disposable component is attempted to be re-used, when it should have been discarded. In some embodiments, the markings improve identification in any type of detection system including, but not limited to, MRI, CT, and ultrasound detection.

The energy delivery systems of the present invention are not limited to particular types of tracking devices. In some embodiments, GPS and GPS related devices are used. In some embodiments, RFID and RFID related devices are used. In some embodiments, barcodes are used.

In such embodiments, authorization (e.g., entry of a code, scanning of a barcode) prior to use of a device with an identification element is required prior to the use of such a device. In some embodiments, the information element identifies that a components has been used before and sends information to the processor to lock (e.g. block) use of system until a new, sterile component is provided.

VIII. Temperature Monitoring Systems

In some embodiments, the energy delivering systems utilize temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately. In some embodiments, temperatures are monitored at several points along the antenna to estimate ablation status, cooling status or safety checks. In some embodiments, the temperatures monitored at several points along the antenna are used to determine, for example, the geographical characteristics of the ablation zone (e.g., diameter, depth, length, density, width, etc.) (e.g., based upon the tissue type, and the amount of power used in the energy delivery device). In some embodiments, the temperatures monitored at several points along the antenna are used to determine, for example, the status of the procedure (e.g., the end of the procedure).

In some embodiments, temperature is monitored using thermocouples or electromagnetic means through the interstitial antenna. In some embodiments, data collected from temperature monitoring is used to initiate one or more cooling procedures described herein (e.g. coolant flow, lowered power, pulse program, shutoff, etc.).

IX. Procedure Device Hubs

The system may further employ one or more additional components that either directly or indirectly take advantage of or assist the features of other components. For example, in some embodiments, one or more monitoring devices are used to monitor and/or report the function of any one or more components of the system. Additionally, any medical device or system that might be used, directly or indirectly, in conjunction with the devices may be included with the system. Such components include, but are not limited to, sterilization systems, devices, and components, other surgical, diagnostic, or monitoring devices or systems, computer equipment, handbooks, instructions, labels, and guidelines, robotic equipment, and the like.

In some embodiments, the systems employ pumps, reservoirs, tubing, wiring, or other components that provide materials on connectivity of the various components of the systems of the present invention. For example, any type of pump may be used to supply gas or liquid coolants to the antennas of the present invention. Gas or liquid handling tanks containing coolant may be employed in the system. In some embodiments, more than one tank is used such that as one tank becomes empty, additional tanks will be used automatically so as to prevent a disruption in a procedure (e.g., as one $CO_2$ tank is drained empty, a second $CO_2$ tanks is used automatically thereby preventing procedure disruption). In certain embodiments, the energy delivery systems (e.g., the energy delivery device, the processor, the power supply, the imaging system, the temperature adjustment system, the temperature monitoring system, and/or the identification systems) and all related energy delivery system utilization sources (e.g., cables, wires, cords, tubes, pipes providing energy, gas, coolant, liquid, pressure, and communication items) are provided in a manner that reduces undesired presentation problems (e.g., tangling, cluttering, and sterility compromise associated with unorganized energy delivery system utilization sources). The present invention is not limited to a particular manner of providing the energy delivery systems and energy delivery system utilization sources such that undesired presentation problems are reduced.

In some embodiments, a procedure device hub is employed that organizes and centralizes cables and minimizes clutter, while centralizes and consolidates control features. For example, an import/export box may be used. In some embodiments, the import/export box contains the power supply and coolant supply. In some embodiments, the import/export box is located outside of a sterile field in which the patient is being treated. In some embodiments, the import/export box is located outside of the room in which the patient is being treated. In some embodiments, one or more cables connect the import/export box to a procedure device pod, which in turn is connected to and supplies energy and coolant to an energy delivery device. In some embodiments, a single cable is used (e.g., a transport sheath). For example, in some such embodiments, a transport sheath contains components for delivery of both energy and coolant to and/or from the import/export box. In some embodiments, the transport sheath connects to the procedure device pod without causing a physical obstacle for medical practitioners (e.g., travels under the floor, overhead, etc). In some embodiments, the cable is a low-loss cable (e.g., a low-loss cable attaching the power supply to the procedure device hub). In some embodiments, the low-loss cable is secured (e.g., to the procedure device hub, to a procedure table, to a ceiling) so as to prevent injury in the event of accidental pulling of the cable. In some embodiments, the cable connecting the power generator (e.g., microwave power generator) and the procedure device hub is low-loss reusable cable. In some embodiments, the cable connecting the procedure device hub to the energy delivery device is flexible disposable cable. In some embodiments, a CERTUS 140 microwave ablation system (NeuWave Medical, Madison, Wis.) is employed.

The present invention is not limited to a particular type or kind of procedure device pod. In some embodiments, the procedure device pod is configured to receive power, coolant, or other elements from the import/export box or other sources. In some embodiments, the procedure device pod provides a control center, located physically near the patient, for any one or more of: delivering energy to a medical device, circulating coolant to a medical device, collecting and processing data (e.g., imaging data, energy delivery data, safety monitoring data, temperature data, and the like), and providing any other function that facilitates a medical procedure. In some embodiments, the procedure device pod is configured to engage the transport sheath so as to receive the associated energy delivery system utilization sources. In some embodiments, the procedure device pod is configured to receive and distribute the various energy delivery system utilization sources to the applicable devices (e.g., energy delivery devices, imaging systems, temperature adjustment systems, temperature monitoring systems, and/or identification systems). For example, in some embodiments, the procedure device pod is configured to receive microwave energy and coolant from energy delivery system utilization sources and distribute the microwave energy and coolant to an energy delivery device. In some embodiments, the procedure device pod is configured to turn on or off, calibrate, and adjust (e.g., automatically or manually) the amount of a particular energy delivery system utilization source as desired. In some embodiments, the procedure device pod has therein a power splitter for adjusting (e.g., manually or automatically turning on, turning off, calibrating) the amount of a particular energy delivery system utilization source as desired. In some embodiments, the procedure device pod has therein software designed to provide energy delivery system utilization sources in a desired manner. In some embodiments, the procedure device pod has a display region indicating associated characteristics for each energy delivery system utilization source (e.g., which devices are presently being used/not used, the temperature for a particular body region, the amount of gas present in a particular $CO_2$ tank, etc.). In some embodiments, the display region has touch capability (e.g., a touch screen). In some embodiments, the processor associated with the energy delivery system is located in the procedure device pod. In some embodiments, the power supply associated with the energy delivery systems is located within the procedure device pod. In some embodiments, the procedure device pod has a sensor configured to automatically inhibit one or more energy delivery system utilization sources upon the occurrence of an undesired event (e.g., undesired heating, undesired leak, undesired change in pressure, etc.). In some embodiments, the weight of the procedure device hub is such that it could be placed onto a patient without causing discomfort and/or harm to the patient (e.g., less than 15 pounds, less than 10 pounds, less than 5 pounds).

Figure 7:
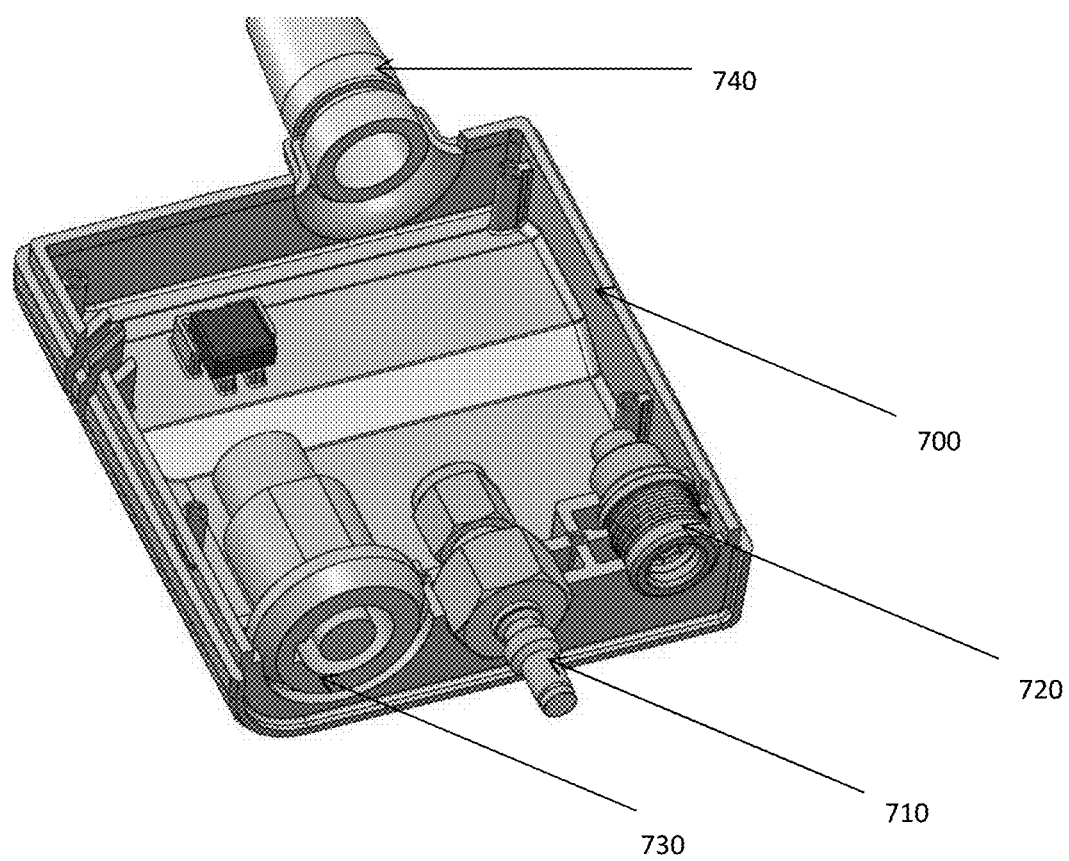
FIG. 7 shows an exemplary interface for connecting an energy delivery device to power and coolant sources.

FIG. 7 provides an example of a component of a pod for connecting an energy delivery device to energy and coolant supplies. The component contains a housing 700 (shown in cutaway to reveal the internal components). A coolant connection component 710 supply (e.g., Swagelok, SS-QM2-S-100 for quick connection) extends out of the housing to connect to a coolant. An ablative energy connection component 720 (e.g., a QMA connector for quick connection) extends out of the housing to connect to a generator. An electrical connection component 730 extends out of the housing to connect to an electrical source. A strain relief 740 is provided through which the proximal end of an energy delivery device cable is inserted and connected to the energy and coolant supplies.

In some embodiments, a hollow inner conductor of the energy delivery device is directly coupled with the coolant connection component 710 (e.g., soldered together). In some such embodiments, the ablative energy source is also coupled to the coolant connection component 710 by a cable that attaches on one end to the interior end of the energy connection component 720 and on the other end to the inner conductor through the coolant connection component 710. As such, both the coolant and energy are linked together in the same interconnector (710). In some such embodiments, the energy cable attaches to the inner conductor at a right angle at a distance of ¼ wavelength from its end. As such, a wave reflected back is cancelled out, preventing energy from reflecting back.

In some embodiments, the housing 700 further comprises a pressure sensor (not shown). The pressure sensor monitors coolant flow via any desired mechanism (e.g., flow sensor; pressure sensor; differential analysis at two different points; flow change at one point; etc.). In the event that aberrant coolant flow is identified, an alarm is triggered and/or system parameters are automatically altered (e.g., power off, coolant off).

In some embodiments, the procedure device pod is designed for location within a sterile setting. In some embodiments, the procedure device pod is positioned on a patient's bed, a table that the patient is on (e.g., a table used for CT imaging, ultrasound imaging, MRI imaging, etc.), or other structure near the patient (e.g., the CT gantry). In some embodiments, the procedure device pod is positioned on a separate table. In some embodiments, the procedure device pod is attached to a ceiling. In some embodiments, the procedure device pod is attached to a ceiling such that a user (e.g., a physician) may move it into a desired position (thereby avoiding having to position the energy delivery system utilization sources (e.g., cables, wires, cords, tubes, pipes providing energy, gas, coolant, liquid, pressure, and communication items) on or near a patient while in use). In some embodiments, the procedure device hub is positioned to lay on a patient (e.g., on a patient's legs, thighs, waist, chest). In some embodiments, the procedure device hub is positioned above a patient's head or below a patient's feet. In some embodiments, the procedure device hub has Velcro permitting attachment onto a desired region (e.g., a procedure table, a patient's drape and/or gown).

In some embodiments, the procedure device hub is configured for attachment to a procedure strap used for medical procedures (e.g., a CT safety strap). In some embodiments, the procedure strap attaches to a procedure table (e.g., a CT table) (e.g., through a slot on the sides of the procedure table, through Velcro, through adhesive, through suction) and is used to secure a patient to the procedure table (e.g., through wrapping around the patient and connecting with, for example, Velcro). The procedure device hub is not limited to a particular manner of attachment with a procedure strap. In some embodiments, the procedure device hub is attached to the procedure strap. In some embodiments, the procedure device hub is attached to a separate strap permitting replacement of the procedure strap. In some embodiments, the procedure device hub is attached to a separate strap configured to attach to the procedure strap. In some embodiments, the procedure device hub is attached to a separate strap configured to attach to any region of the procedure table. In some embodiments, the procedure device hub is attached to a separate strap having insulation and/or padding to ensure patient comfort.

In some embodiments, the procedure device hub is configured for attachment to a procedure ring. The present invention is not limited to a particular type or kind of procedure ring. In some embodiments, the procedure ring is configured for placement around a patient (e.g., around a patient's torso, head, feet, arm, etc.). In some embodiments, the procedure ring is configured to attach to a procedure table (e.g., a CT table). The procedure device ring is not limited to a particular shape. In some embodiments, the procedure device ring is, for example, oval, circular, rectangular, diagonal, etc. In some embodiments, the procedure device ring is approximately half of a cyclical shape (e.g., 25% of a cyclical shape, 40% of a cyclical shape, 45% of a cyclical shape, 50% of a cyclical shape, 55 of a cyclical shape, 60 of a cyclical shape, 75 of a cyclical shape). In some embodiments, the procedure ring is, for example, metal, plastic, graphite, wood, ceramic, or any combination thereof. The procedure device hub is not limited to a particular manner of attachment to the procedure ring. In some embodiments, the procedure device hub attaches onto the procedure ring (e.g., with Velcro, with snap-ons, with an adhesive agent). In some embodiments utilizing low-loss cables, the low-loss cables additional attach onto the procedure ring. In some embodiments, the size of the procedure ring can be adjusted (e.g., retracted, extended) to accommodate the size of a patient. In some embodiments, additional items may be attached to the procedure ring. In some embodiments, the procedure ring may be easily moved to and from the vicinity of a patient.

In some embodiments, the procedure device hub is configured for attachment onto a custom sterile drape. The present invention is not limited to a particular type or kind of custom sterile drape. In some embodiments, the custom sterile drape is configured for placement onto a patient (e.g., onto a patient's torso, head, feet, arm, entire body, etc.). In some embodiments, the custom sterile drape is configured to attach to a procedure table (e.g., a CT table). The custom sterile drape is not limited to a particular shape. In some embodiments, the custom sterile drape is, for example, oval, circular, rectangular, diagonal, etc. In some embodiments, the shape of the custom sterile drape is such that it accommodates a particular body region of a patient. In some embodiments, the procedure ring is, for example, cloth, plastic, or any combination thereof. The procedure device hub is not limited to a particular manner of attachment to the custom sterile drape. In some embodiments, the procedure device hub attaches onto the custom sterile drape (e.g., with Velcro, with snap-ons, with an adhesive agent, clamps (e.g., alligator clamps)). In some embodiments utilizing low-loss cables, the low-loss cables additional attach onto the custom sterile drape. In some embodiments, additional items may be attached to the custom sterile drape. In some embodiments, the custom sterile drape may be easily moved to and from the vicinity of a patient. In some embodiments, the custom sterile drape has one more fenestrations for purposes of performing medical procedures.

In some embodiments, the procedure device hub is configured with legs for positioning the hub in the vicinity of a patient. In some embodiments, the procedure device hub has adjustable legs (e.g., thereby allowing positioning of the procedure device hub in a variety of positions). In some embodiments, the procedure device hub has three adjustable legs thereby allowing the device to be positioned in various tri-pod positions. In some embodiments, the legs have therein Velcro permitting attachment onto a desired region (e.g., a procedure table, a patient's drape and/or gown). In some embodiments, the legs are formed from a springy material configured to form an arc over the procedure table (e.g., CT table) and squeeze the rails of the procedure table. In some embodiments, the legs are configured to attach onto the rails of the procedure table. In some embodiments, the procedure hub is attached directly or indirectly to an arm, which may be connected to a bed frame or procedure table rail.

In some embodiments, the procedure device pod is configured to communicate (wirelessly or via wire) with a processor (e.g., a computer, with the Internet, with a cellular phone, with a PDA). In some embodiments, the procedure device hub may be operated via remote control. In some embodiments, the procedure device pod has thereon one or more lights. In some embodiments, the procedure device hub provides a detectable signal (e.g., auditory, visual (e.g., pulsing light)) when power is flowing from the procedure device hub to an energy delivery device. In some embodiments, the procedure device hub has an auditory input (e.g., an MP3 player). In some embodiments, the procedure device hub has speakers for providing sound (e.g., sound from an MP3 player). In some embodiments, the procedure device hub has an auditory output for providing sound to an external speaker system. In some embodiments, the use of a procedure device pod permits the use of shorter cables, wires, cords, tubes, and/or pipes (e.g., less than 4 feet, 3 feet, 2 feet). In some embodiments, the procedure device pod and/or one more components connected to it, or portions thereof are covered by a sterile sheath. In some embodiments, the procedure device hub has a power amplifier for supplying power (e.g., to an energy delivery device).

In some embodiments, the procedure device pod is configured to compress transported coolants (e.g., $CO_2$) at any desired pressure so as to, for example, retain the coolant at a desired pressure (e.g., the critical point for a gas) so as to improve cooling or temperature maintenance. For example, in some embodiments, a gas is provided at or near its critical point for the purpose of maintaining a temperature of a device, line, cable, or other component at or near a constant, defined temperature. In some such embodiments, a component is not cooled per se, in that its temperature does not drop from a starting temperature (e.g., room temperature), but instead is maintained at a constant temperature that is cooler than where the component would be, but for the intervention. For example, $CO_2$ may be used at or near its critical point (e.g., 31.1 Celsius at 78.21 kPa) to maintain temperature so that components of the system are sufficiently cool enough not to burn tissue, but likewise are not cooled or maintained significantly below room temperature or body temperature such skin in contact with the component freezes or is otherwise damaged by cold. Using such configurations permits the use of less insulation, as there are not "cold" components that must be shielded from people or from the ambient environment. In some embodiments, the procedure device pod has a retracting element designed to recoil used and/or unused cables, wires, cords, tubes, and pipes providing energy, gas, coolant, liquid, pressure, and/or communication items. In some embodiments, the procedure device pod is configured to prime coolants for distribution into, for example, an energy delivery device such that the coolant is at a desired temperature prior to use of the energy delivery device. In some embodiments, the procedure device pod has therein software configured to prime coolants for distribution into, for example, an energy delivery device such that the system is at a desired temperature prior to use of the energy delivery device. In some embodiments, the circulation of coolants at or near critical point permits cooling of the electronic elements of the energy delivery devices without having to use additional cooling mechanisms (e.g., fans).

In one illustrative embodiment, an import/export box contains one or more microwave power sources and a coolant supply (e.g., pressurized carbon dioxide gas). This import/export box is connected to a single transport sheath that delivers both the microwave energy and coolant to a procedure device pod. The coolant line or the energy line within the transport sheath may be wound around one another to permit maximum cooling of the transport sheath itself. The transport sheath is run into the sterile field where a procedure is to take place along the floor in a location that does not interfere with the movement of the medical team attending to the patient. The transport sheath connects to a table located near an imaging table upon which a patient lays. The table is portable (e.g., on wheels) and connectable to the imaging table so that they move together. The table contains arm, which may be flexible or telescoping, so as to permit positioning of the arm above and over the patient. The transport sheath, or cables connected to the transport sheath, run along the arm to the overhead position. At the end of the arm is the procedure device pod. In some embodiments, two or more arms are provided with two or more procedure device pods or two or more sub-components of a single procedure device pod. The procedure device pod is small (e.g., less than 1 foot cube, less than 10 cm cube, etc.) to allow easy movement and positioning above the patient. The procedure device pod contains a processor for controlling all computing aspects of the system. The device pod contains one or more connections ports for connecting cables that lead to energy delivery devices. Cables are connected to the ports. The cables are retractable and less than three feet in length. Use of short cables reduces expense and prevents power loss. When not in use, the cables hang in the air above the patient, out of contact with the patient's body. The ports are configured with a dummy load when not in use (e.g., when an energy delivery device is not connected to a particular port). The procedure device pod is within reach of the treating physician so that computer controls can be adjusted and displayed information can be viewed, in real-time, during a procedure.

X. Uses for Energy Delivery Systems

The systems of the present invention are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the present invention provides systems that access to a difficult to reach region of the body (e.g. the periphery or central regions of the lungs). In some embodiments, the system navigates through a branched body structure (e.g. bronchial tree) to reach a target site. In some embodiments, systems, devices, and methods provide delivery of energy (e.g. microwave energy, energy for tissue ablation) to difficult to reach regions of a body, organ, or tissue (e.g. the periphery or central region of the lungs). In some embodiments, the system delivers energy (e.g. microwave energy, energy for tissue ablation) to a target site though a branched structure (e.g. bronchial tree). In some embodiments, the system delivers energy (e.g. microwave energy, energy for tissue ablation) to the periphery or central region of the lungs through the bronchi (e.g. primary bronchi, secondary bronchi, tertiary bronchi, bronchioles, etc.). In some embodiments, accessing the lungs through the bronchi provides a precise and accurate approach while minimizing collateral damage to the lungs. Accessing the lung (e.g. central lung or lung periphery) from outside the lung requires puncturing or cutting the lung, which can be avoided by bronchial access.

In some embodiments, a primary catheter (e.g. endoscope, bronchoscope, etc.), containing a channel catheter and steerable navigation catheter is advanced into the bronchial tree (e.g. via the trachea) until the decreasing circumference of the bronchi will not allow further advancement of the primary catheter. In some embodiments, a primary catheter (e.g. endoscope, bronchoscope, etc.), containing a channel catheter and steerable navigation catheter is advanced into the bronchial tree (e.g. via the trachea) up to the desired point for deployment of the channel catheter. In some embodiments, the primary catheter is advanced into the trachea, primary bronchi, and/or secondary bronchi, but not further. In some embodiments, a channel catheter containing a steerable navigation catheter is advanced through the primary catheter, and beyond the distal tip of the primary catheter, into the bronchial tree (e.g. via the trachea, via the primary bronchi, via secondary bronchi, via tertiary bronchi, via bronchioles, etc.) up to the target location (e.g. treatment site, tumor, etc.). In some embodiments, a channel catheter containing a steerable navigation catheter is advanced into the bronchial tree (e.g. via the trachea, primary bronchi, etc.) until the decreasing size of the bronchi will not allow further advancement (e.g. in the tertiary bronchi, in the bronchioles, at the treatment site). In some embodiments, the channel catheter is advanced into the trachea, primary bronchi, secondary bronchi, tertiary bronchi, and/or bronchioles. In some embodiments, the steerable navigation catheter is advanced into the trachea, primary bronchi, secondary bronchi, tertiary bronchi, and/or bronchioles to the treatment site. In some embodiments, the steerable navigation catheter is withdrawn through the channel catheter, leaving the open channel lumen extending from the point of insertion (e.g. into the subject, into the trachea, into the bronchial tree, etc.), through the bronchial tree (e.g. through the trachea, primary bronchi, secondary bronchi, tertiary bronchi, bronchioles, etc.) to the target site (e.g. treatment site, tumor, central or peripheral lunch tumor). In some embodiments, an energy delivery device (e.g. microwave ablation device) is inserted through the open channel lumen to access the target site. In some embodiments, the present invention provides systems, devices, and method to access central or peripheral lung tumors through the bronchial tree with a microwave ablation device.

In some embodiments, transbronchial treatment is employed. In such embodiments, the devices are positioned through the airways (e.g., following bronchial tree) to the best straight line or other desired path to the target. The airway wall is then pierced and the device is advanced in proximity to the target to facilitate ablation.

In some embodiments, the present invention provides systems, methods, and devices for placement of an energy delivery device at a difficult to access tissue region within a subject. In some embodiments, the present invention provides placement of an energy delivery device for tissue ablation therapy (e.g. tumor ablation). In some embodiments, the present invention provides access to, and/or treatment of, tumors, growths, and/or nodules on the periphery of the lungs or in the central lungs. In some embodiments, the present invention provides access to, and ablation of, peripheral pulmonary nodules. Peripheral pulmonary nodules and central nodules are difficult to access through the bronchial tree because of their location near the tertiary bronchi and bronchioles, beyond the reach of conventional devices and techniques. In some embodiments, devices, systems, and methods of the present invention provide access to central and peripheral pulmonary nodules through the bronchial tree. Peripheral pulmonary nodules are generally less than 25 mm in diameter (e.g. <25 mm, <20 mm, <10 mm, <5 mm, <2 mm, <1 mm, etc.). In some embodiments, peripheral pulmonary nodules are 0.1 mm-25 mm in diameter (e.g. 0.1 mm . . . 0.2 mm . . . 0.5 mm . . . 1.0 mm . . . 1.4 mm . . . 2.0 mm . . . 5.0 mm . . . 10 mm . . . 20 mm . . . 25 mm, and diameters therein). In some embodiments, the present invention provides access and treatment of tumors, growths, and nodules of any size and any location within a subject (e.g. within the lungs of a subject). In some embodiments, the present invention provides curative treatment and/or palliative treatment of tumors (e.g. nodules) in the central or peripheral lung.

XI. Device Placement Systems

In some embodiments, the present invention provides a primary catheter (e.g. endoscope, bronchoscope, etc.). In some embodiments, any suitable endoscope or bronchoscope known to those in the art finds use as a primary catheter in the present invention. In some embodiments, a primary catheter adopts characteristics of one or more endoscopes and/or bronchoscopes known in the art, as well as characteristics described herein. One type of conventional flexible bronchoscope is described in U.S. Pat. No. 4,880,015, herein incorporated by reference in its entirety. The bronchoscope measures 790 mm in length and has two main parts, a working head and an insertion tube. The working head contains an eyepiece; an ocular lens with a diopter adjusting ring; attachments for suction tubing, a suction valve, and light source; and an access port or biopsy inlet, through which various devices and fluids can be passed into the working channel and out the distal end of the bronchoscope. The working head is attached to the insertion tube, which typically measures 580 mm in length and 6.3 mm in diameter. The insertion tube contains fiberoptic bundles, which terminate in the objective lens at the distal tip, light guides, and a working channel. Other endoscopes and bronchoscopes which may find use in embodiments of the present invention, or portions of which may find use with the present invention, are described in U.S. Pat. Nos. 7,473,219; 6,086,529; 4,586,491; 7,263,997; 7,233,820; and 6,174,307.

In some embodiments, the present invention provides a channel catheter (a.k.a. guide catheter, sheath, sheath catheter, etc.). In some embodiments, a guide catheter is configured to fit within the lumen of a primary catheter and contains a channel lumen of sufficient diameter (e.g. 1 mm . . . 2 mm . . . 3 mm . . . 4 mm . . . 5 mm) to accommodate a steerable navigation catheter and/or one or more suitable tools (e.g. energy delivery device). In some embodiments, a channel catheter is of sufficient length to extend from an insertion site (e.g. mouth, incision into body of subject, etc.) through the trachea and/or bronchial tree to a treatment site in the central or peripheral lung (e.g. 50 cm . . . 75 cm . . . 1 m . . . 1.5 m . . . 2 m). In some embodiments, a channel catheter is of sufficient length to extend beyond the reach of a primary catheter to reach a treatment site (e.g. central or peripheral lung tissue). In some embodiments, a channel catheter is highly flexible to access a circuitous route through a subject (e.g. through a branched structure, through the bronchial tree, etc.). In some embodiments, a channel catheter is constructed of braided material to provide both strength and flexibility, as is understood in the art. In some embodiments, a channel catheter comprises the outer conductor of a triaxial or coaxial transmission line. In some embodiments, a channel catheter comprises a navigation and/or steering mechanism. In some embodiments, a channel catheter is without an independent means of navigation, position recognition, or maneuvering. In some embodiments, a channel catheter relies upon the primary catheter or steerable navigation catheter for placement.

In some embodiments, the present invention provides a steerable navigation catheter. In some embodiments, a steerable navigation catheter is configured to fit within the lumen of a channel catheter. In some embodiments, a steerable navigation catheter has a similar diameter to energy transmission lines described herein (e.g. 0.2 mm . . . 0.5 mm . . . 1.0 mm . . . 1.5 mm . . . 2.0 mm). In some embodiments, a steerable navigation catheter is of sufficient length to extend from an insertion site (e.g. mouth, incision into body of subject, etc.) to a treatment site (e.g. through the trachea and/or bronchial tree to a treatment site in the central or peripheral lung (e.g. 50 cm . . . 75 cm . . . 1 m . . . 1.5 m . . . 2 m). In some embodiments, a channel catheter is of sufficient length to extend beyond the reach of a primary catheter to reach a treatment site (e.g. central or peripheral lung tissue). In some embodiments, a steerable navigation catheter engages a channel catheter such that movement of the steerable navigation catheter results in synchronous movement of the channel catheter. In some embodiments, as a steerable navigation catheter is inserted along a path in a subject, the channel catheter surrounding the steerable navigation catheter moves with it. In some embodiments, a channel catheter is placed within a subject by a steerable navigation catheter. In some embodiments, a steerable navigation catheter can be disengaged from a channel catheter. In some embodiments, disengagement of a steerable navigation catheter and channel catheter allows movement of the steerable navigation catheter further along a pathway without movement of the channel catheter. In some embodiments, disengagement of a steerable navigation catheter and channel catheter allows retraction of the steerable navigation catheter through the channel catheter without movement of the channel catheter.

In some embodiments, all inserted components of a system or device are configured for movement along a narrow and circuitous path through a subject (e.g. through a branched structure, through the bronchial tree, etc.). In some embodiment, components comprise a flexible material configured for tight turning radiuses. In some embodiment, necessarily rigid components are reduced in size (e.g. short length) to allow for tight turning radiuses.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A device for delivering microwave energy to a distant region of a body, comprising:
   a) a proximal end connectable to a microwave energy generator and a coolant source;
   b) a distal end configured to generate ablative energy in a defined region surrounding said distal end;
   c) an inner conductor;
   d) a central region comprising
      a non-conductive core surrounding the inner conductor such that an air channel is between the non-conductive core and the inner conductor, and
      a monofilament tube wound spirally around said inner conductor such that there is 1) no gap through the monofilament tube, 2) no gap between the monofilament tube and the inner conductor and 3) no gap between the monofilament tube and the non-conductive core;
   e) an outer conductor surrounding said non-conductive core; and
   f) a coolant flow exchanger at the distal end configured to receive coolant from said inner conductor and return said coolant through said air channel.

2. The device of claim 1, wherein the diameter of the device is sized for endobronchial delivery of microwave energy to a central or peripheral lung nodule.

3. The device of claim 1 wherein the diameter of the device is less than 3 mm.

4. The device of claim 1, wherein the diameter of the device is less than 1.4 mm.

5. The device of claim 1, wherein the outer conductor comprises biaxially-oriented polyethylene terephthalate.

6. The device of claim 1, wherein the inner conductor is hollow.

7. The device of claim 1, wherein the outer conductor comprises a flexible and/or collapsible material.

8. The device of claim 7, wherein the flexible and/or collapsible material renders the device capable of circuitous navigation through a subject.

9. The device of claim 8, wherein the flexible and/or collapsible material renders the device capable of circuitous navigation through a subject without undesired heating of tissue regions along the circuitous navigation.

10. The device of claim 8, wherein the flexible and/or collapsible material renders the device capable of circuitous navigation through a subject without undesired tissue damage of tissue regions along the circuitous navigation.

11. The device of claim 8, wherein the device is capable of endobronchial navigation and/or transbronchial navigation.

12. A system comprising the device of claim 1 and one or more of a delivery tube, a microwave generator, a coolant supply, a control computer, an imaging device, and a power and coolant interface.

13. The system of claim 12, wherein said coolant supply comprises a pressurized gas.

14. The system of claim 13, wherein said pressurized gas is $CO_2$.

15. The system of claim 12, wherein said coolant supply delivers coolant through said inner conductor of said device at zero to 1000 psi.

16. The system of claim 12, wherein said interface comprises: a) a gas connector for connecting to a coolant source; b) a power connector for connecting to an electrical source; and c) an ablative power connector for connecting to a microwave generator.

17. A method of ablating a tissue comprising: positioning the distal end of said device of claim 1 near a target tissue and applying ablative energy from said device.

18. The method of claim 17, wherein said target tissue is in a lung.

19. The method of claim 18, wherein said device is positioned endobronchially or transbronchially.

20. The method of claim 19, wherein said target tissue is a central or peripheral lung nodule.

\* \* \* \* \*